(12) United States Patent
De Waziers et al.

(10) Patent No.: US 9,243,231 B2
(45) Date of Patent: Jan. 26, 2016

(54) MUTANT CYTOCHROME P450 2B6 PROTEINS AND USES THEREOF

(75) Inventors: Isabelle De Waziers, Paris (FR); Walid Touati, Paris (FR); Monique Diry, Paris (FR); Jean-Pierre Flinois, Paris (FR); Patrick Dansette, Paris (FR); Philippe Beaune, Paris (FR)

(73) Assignee: Institut National de la Santé et de la Recherche Médicale (INSERM), Paris (FR)

( * ) Notice: Subject to any disclaimer, the term of this patent is extended or adjusted under 35 U.S.C. 154(b) by 16 days.

(21) Appl. No.: 14/115,639

(22) PCT Filed: May 4, 2012

(86) PCT No.: PCT/EP2012/058219
§ 371 (c)(1),
(2), (4) Date: Jan. 9, 2014

(87) PCT Pub. No.: WO2012/150326
PCT Pub. Date: Nov. 8, 2012

(65) Prior Publication Data
US 2014/0127180 A1 May 8, 2014

(30) Foreign Application Priority Data
May 5, 2011 (EP) ................................... 11305530

(51) Int. Cl.
*A61K 48/00* (2006.01)
*A61K 38/44* (2006.01)
*C07K 14/47* (2006.01)
*C12N 9/02* (2006.01)

(52) U.S. Cl.
CPC ............ *C12N 9/0036* (2013.01); *C12N 9/0042* (2013.01); *C12N 9/0071* (2013.01); *C07K 2319/00* (2013.01)

(58) Field of Classification Search
CPC combination set(s) only.
See application file for complete search history.

(56) References Cited

FOREIGN PATENT DOCUMENTS

WO 01/59152 A2 8/2001

OTHER PUBLICATIONS

Tychopoulos et al (A virus-directed enzyme prodrug therapy (VDEPT) strategy for lung cancer using a CYP2B6/NADPH-cytochrome P450 reductase fusion protein, Cancer Gene Therapy May 2005;12(5):497-508.*
Nguyen et al., "Improvement of cyclophosphamide activation by CYP2B6 mutants: From in silico to ex vivo", Molecular Pharmacology, Apr. 2008, pp. 1122-1133, vol. 73, No. 4.

* cited by examiner

*Primary Examiner* — Kagnew H Gebreyesus
(74) *Attorney, Agent, or Firm* — Whitham, Curtis, Christofferson & Cook, P.C.

(57) ABSTRACT

The present invention to relates mutant human cytochrome P450 2B6 (CYP2B6) proteins, and fusion proteins comprising said mutant CYP2B6 proteins. In particular, fusion proteins comprising mutant CYP2B6 and NAPDH-cytochrome P450 reductase are provided. The invention also relates to methods of treatment of cancer and the use of said proteins and fusion proteins in the treatment of cancer, in particular via virus-directed enzyme prodrug therapy.

11 Claims, 10 Drawing Sheets

```
1   melsvllfla lltgllllv  qrhpnthdrl ppgprplpll gnllqmdrrg llksflrfre
61  kygdvftvhl gprpvvmlcg veairealvd kaeafsgrgk iamvdpffrg ygvvfangnr
121 wkvlrrfsvt tmrdfgmgkr sveeriqeea qclieelrks kgalmdptfl fqsitaniic
181 sivfgkrfhy qdqeflkmmn lfyqtfslis svfgqlfelf sgflkyfpga hrqvyknlqe
241 inayighsve khretldpsa pkdlidtyll hmekeksnah sefshqnlnl ntlslffagt
301 ettsttlryg fllmlkyphv aervyreieq vigphrppel hdrakmpyte aviyeiqrfs
361 dllpmgvphi vtqhtsfrgy iipkdtevfl ilstalhdph yfekpdafnp dhfldangal
421 kkteafipfs lgkriclgeg iaraelflff ttilqnfsma spvapedidl tpqecgwgki
481 pptyqirflp r
```

FIG.1

```
1   minmgdshvd tsstvseava eevslfsmtd milfslivgl ltywflfrkk keevpeftki
61  qtltssvres sfvekmkktg rniivfygsq tgtaeefanr lskdahrygm rgmsadpeey
121 dladlsslpe idnalvvfcm atygegdptd naqdfydwlq etdvdlsgvk favfglgnkt
181 yehfnamgky vdkrleqlga qrifelglgd ddgnleedfi twreqfwpav cehfgveatg
241 eessirqyel vvhtdidaak vymgemgrlk syenqkppfd aknpflaavt tnrklnqgte
301 rhlmhleldi sdskiryesg dhvavypand salvnqlgki lgadldvvms lnnldeesnk
361 khpfpcptsy rtaltyyldi tnpprtnvly elaqyaseps eqellrkmas ssgegkelyl
421 swvvearrhi lailqdcpsl rppidhlcel lprlqaryys iassskvhpn svhicavvve
481 yetkagrink gvatnwlrak epagenggra lvpmfvrksq frlpfkattp vimvgpgtgv
541 apfigfiqer awlrqqgkev getllyygcr rsdedylyre elaqfhrdga ltqlnvafsr
601 eqshkvyvqh llkqdrehlw klieggahiy vcgdarnmar dvqntfydiv aelgamehaq
661 avdyikklmt kgrysldvws
```

FIG.2

```
1    melsvllfla  lltgllllv   qrhpnthdrl  ppgprplpll  gnllqmdrrg  llksflrfre
61   kygdvftvhl  gprpvvmlcg  veairealvd  kaeafsgrgk  iamvdpffrg  ygvvfangnr
121  wkvlrrfsvt  tmrdfgmgkr  sveeriqeea  qclieelrks  kgalmdptfl  fqsitaniic
181  sivfgkrfhy  qdqeflkmmn  lfyqtfslis  svfgqlfelf  sgflkyfpga  hrqvyknlqe
241  inayighsve  khretldpsa  pkdlidtyll  hmekeksnah  sefshqnlnl  ntlslffagt
301  ettsttlryg  fllmlkyphv  aervyreieq  vigphrppel  hdrakmpyte  aviyeiqrfs
361  dllpmgvphi  vtqhtsfrgy  iipkdtevfl  ilstalhdph  yfekpdafnp  dhfldangal
421  kkteafipfs  lgkriclgeg  iaraelflff  ttilqnfsma  spvapedidl  tpqecgwgki
481  pptyqirflp  ssssstsmtd  milfslivgl  ltywflfrkk  keevpeftki  qtltssvres
541  sfvekmkktg  rniivfygsq  tgtaeefanr  lskdahrygm  rgmsadpeey  dladlsslpe
601  idnalvvfcm  atygegdptd  naqdfydwlq  etdvdlsgvk  favfglgnkt  yehfnamgky
661  vdkrleqlga  qrifelglgd  ddgnleedfi  twreqfwpav  cehfgveatg  eessirqyel
721  vvhtdidaak  vymgemgrlk  syenqkppfd  aknpflaavt  tnrklnqgte  rhlmhleldi
781  sdskiryesg  dhvavypand  salvnqlgki  lgadldvvms  lnnldeesnk  khpfpcptsy
841  rtaltyyldi  tnpprtnvly  elaqyaseps  eqellrkmas  ssgegkelyl  swvvearrhi
901  lailqdcpsl  rppidhlcel  lprlqaryys  iassskvhpn  svhicavvve  yetkagrink
961  gvatnwlrak  epagenggra  lvpmfvrksq  frlpfkattp  vimvgpgtgv  apfigfiqer
1021 awlrqqgkev  getllyygcr  rsdedylyre  elaqfhrdga  ltqlnvafsr  eqshkvyvqh
1081 llkqdrehlw  kliegqahiy  vcgdarnmar  dvqntfydiv  aelgamehaq  avdyikklmt
1141 kgrysldv
```

FIG.3

```
1    melsvllfla  lltgllllv   qrhpnthdrl  ppgprplpll  gnllqmdrrg  llksflrfre
  61 kygdvftvhl  gprpvvmlcg  veairealvd  kaeafsgrgk  iamvdpffrg  ygvifangnr
 121 wkvlrrfsvt  tmrdfgmgkr  sveeriqeea  qclieelrks  kgalmdptfl  fqsitaniic
 181 sivfgkrfhy  qdqeflkmln  lfyqtfslis  svfgqlfelf  sgflkyfpga  hrqvyknlqe
 241 inayighsve  khretldpsa  pkdlidtyll  hmekeksnah  sefshqnlnl  ntlslffagt
 301 ettsttlryg  fllmlkyphv  aervyreieq  vigphrppel  hdrakmpyte  aviyeiqrfs
 361 dllpmgvphi  vtqhtsfrgy  iipkdtevfl  ilstalhdph  yfekpdafnp  dhfldangal
 421 kkteafipfs  lgkriclgeg  iaraelflff  ttilqnfsma  spvapedidl  tpqecgvgki
 481 pptyqirflp  r
```

FIG.4

MUTANT CYTOCHROME P450 2B6 PROTEINS AND USES THEREOF

FIELD OF THE INVENTION

The present invention concerns mutant human cytochrome P450 2B6 (CYP2B6) proteins, and fusion proteins comprising said mutant CYP2B6 proteins. The invention also relates to the use of said proteins and fusion proteins in the treatment of cancer and other diseases, in particular via enzyme prodrug therapy, as well as methods of treatment of cancer and other diseases.

BACKGROUND

The cytochrome P450 (CYP) family of enzymes is a diverse group of enzymes most of which catalyse the oxidation of organic substances, including metabolic intermediates and toxins such as drugs. CYPs catalyse oxidation reactions via electron transfer from NADPH by a reductase, usually NADPH-cytochrome P450 reductase.

CYPs are the main enzymes involved in drug metabolism and bioactivation. They have thus found use in enzyme prodrug therapy, a tumour therapy aimed at reducing the systemic side-effects of antitumour medication. Medication is administered as a noncytotoxic prodrug and converted to its active form by drug-metabolising enzymes which are targeted to the tumour cells. Generally, tumour cells are transfected with a gene encoding the enzyme which is capable of bioactivating the inactive prodrug, followed by treatment of the patient with the prodrug (gene-directed enzyme prodrug therapy or GDEPT). Viral vectors are often used for transgene introduction, a strategy known as virus-directed enzyme prodrug therapy (VDEPT). This strategy can increase both the specificity and sensitivity of drug treatment, thus reducing side effects and improving efficacy.

CYP2B6 metabolises a range of toxic substances, including nicotine and the anticancer drugs cyclophosphamide, ifosfamide and thiotepa. Because of this activity, CYP2B6 has been used in models of VDEPT using the chemotherapeutic agent cyclophosphamide (CPA), which requires activation by CYP2B6 in order to render it cytotoxic. In patients treated with CPA in the standard way, activation by CYP2B6 occurs in the liver, and the active drug is then transported to the tumour site via the blood stream. Such non-specific administration can cause serious side effects due to cytotoxic activity on non-tumour cells, including cardiotoxicity, renal toxicity, bone marrow suppression and neurotoxicity. CYP2B6 is thus an ideal candidate for VDEPT, and has been successfully used in in vivo models of VDEPT using cytotoxicity assays (Waxman et al, Drug Metab Rev 1999, 31: 503-522; Tychopoulos et al, Cancer Gene Ther 2005, 12: 497-508).

One of the disadvantages of using CYP2B6 in a VDEPT strategy is the relatively low affinity of CYP2B6 for CPA, which shows a high $K_m$. Modification of the CYP2B6 enzyme to increase its catalytic efficiency ($V_{max}/K_m$) for 4-hydroxylation of CPA has therefore been attempted, in order to improve the therapeutic effect of CYPB26 when used in VDEPT. The inventors have previously produced a double active site mutant (I114V/V477W) by mutagenesis of the active site of CYPB26 which had a four-fold increase in CPA-4-hydroxlation efficiency compared to the wild-type enzyme, mainly as a result of an increase in enzyme affinity (Nguyen et al, Mol Pharmacol 2008, 73: 1122-1133).

Another possibility for improving the efficiency of CYP2B6-mediated VDEPT is to co-transfect tumour cells with NADPH cytochrome P450 reductase (RED) in order to supply CYP2B6 with electrons, as basal cellular reductase activity may be insufficient and may thus be a limiting factor for CYP2B6 activity. Earlier work by the inventors has shown that supplying external RED in this way can increase CYP2B6-mediated toxicity. Two approaches were successfully used to supplement intratumoral RED activity and increase CYP2B6 activity: co-transfection of separate RED and CYB2B6 proteins, and creation of a CYP2B6-RED fusion protein which has both 4-hydroxylase activity and reductase activity (Tychopoulos et al, Cancer Gene Ther 2005, 12: 497-508).

These studies have shown that there is scope for improving the efficiency of CYP2B6 when used in enzyme-directed prodrug therapy. Such improvement could permit known drugs to be used on new tumour targets, as well as improving the response of known targets to drug therapy. Modulation of CYP2B6 activity is thus of great potential clinical importance and represents a useful potential tool in treating cancer.

SUMMARY OF THE INVENTION

The inventors have produced a novel mutant human CYP2B6 protein which has an affinity for CPA 8 times greater than that of the wild-type enzyme, while retaining the same $V_{max}$. The mutant was obtained by mutating isoleucine at position 114 to valine, leucine at position 199 to methionine and valine at position 477 to tryptophan. The inventors have demonstrated that the mutant protein retains its activity when produced as part of a fusion protein with NADPH cytochrome p450 reductase fusion protein, and that the fusion protein can confer cytotoxic activity on CPA against tumour cell lines which do not response to CPA alone. They have also shown that the linker of the fusion protein can play a role in enhancing the effectiveness of the fusion protein; in particular by improving reductase activity.

The CYP2B6 triple mutant protein created by the inventors was 10 times more efficient at metablolising CPA into cytotoxic metabolite than the wild-type protein, a far greater improvement than that obtained with the double mutant previously reported. The triple mutant very efficiently sensitised CPA-resistant tumour cells to CPA and resulted dramatic reductions in tumour size in animal models. The triple mutant may thus be used to render drug-resistant tumours sensitive to treatment and to reduce the amount of drug required for effective tumour treatment, reducing the risk of side effects.

Thus, the invention provides a CYP2B6 protein having the amino acid sequence of FIG. 1 (SEQ ID No 1), or a variant or fragment thereof, wherein said variant or fragment comprises residues 114V, 199M and 477W as shown in FIG. 1 (SEQ ID No 1). Preferably, said variant or fragment retains a biological activity of a protein having the full-length amino acid sequence of FIG. 1 (SEQ ID No 1).

Also provided is a fusion protein comprising (i) a CYP2B6 protein of the invention as defined herein, and (ii) a NADPH-cytochrome P450 reductase protein as defined herein. In a preferred embodiment, said CYP2B6 protein comprises amino acids 1-490 of the amino acid sequence shown in FIG. 1 (SEQ ID No 1), and/or said NADPH-cytochrome P450 reductase comprises amino acids 57-678 of FIG. 2 (SEQ ID No 2). In one embodiment, the CYP2B6 protein is upstream of the NADPH-cytochrome P450 reductase. In some embodiments, the proteins are separated by a linker, preferably a polypeptide linker. In some embodiments, the linker comprises $Ser_n Thr$, wherein n may be 1 to 7, optionally 3, optionally 5.

Also provided is an isolated nucleic acid encoding any of the proteins disclosed herein, including all disclosed variants, fragments and fusion proteins.

Also provided is a vector comprising said nucleic acid, for example an expression vector and/or a vector capable of transfecting of infecting a host cell such as a tumour cell. Suitable vectors include RNA, DNA, viral and retroviral vectors.

Further provided is a host cell comprising said vector. A host cell may be, for example, a bacterial, yeast, mammalian or plant cell. Where the cell is a mammalian cell, said cell is preferably not comprised within a human body.

Also provided is a method of making a fusion protein as disclosed herein, comprising culturing said host cell conditions suitable for expression of said protein, and optionally purifying said protein from the cell culture.

Also provided is a protein, fusion protein or vector of the invention for use in a method of treatment of the human or animal body. The treatment may be treatment of cancer, for example cancer of the head and neck, leukaemia, lymphoma, gliosarcoma, pancreatic cancer, breast cancer and melanoma. In preferred embodiments, said protein or vector is administered in combination with a chemotherapeutic agent, either simultaneously or sequentially. Preferably, the chemotherapeutic agent is administered in prodrug form.

Further provided is a method of treatment of cancer comprising administering a protein, fusion protein or vector of the invention, to a patient, preferably a patient in need thereof, in combination with a chemotherapeutic agent, either sequentially or simultaneously. Preferably, the chemotherapeutic agent is administered in prodrug form.

Enzyme Prodrug Therapy

The proteins of the invention may find use in enzyme prodrug therapy, including antibody-directed prodrug therapy (ADEPT), and gene-directed prodrug therapy (GDEPT) such as virus-directed enzyme prodrug therapy (VDEPT). The principle of these different approaches is identical: an chemotherapeutic agent is administered in an inactive prodrug form, and converted within the body to active drug by an enzyme which is targetted to tumour cells. In GDEPT, tumour cells are transfected with a vector, such as a virus, which expresses the desired enzyme within the tumour cells. In ADEPT, the enzyme is delivered to tumour cells by linkage to a targeting antibody which preferentially binds to tumour cells. Once the prodrug has been converted to active drug by the targeted enzyme, it can then diffuse to neighbouring cells to exert its effect.

VDEPT is carried out using a virus which can infect tumour cells. Such viruses may include retroviruses, preferably viruses which referentially infect dividing cells, as detailed below.

Alternatively, the enzyme of interest may be expressed under control of a transcriptional regulatory sequence whose expression is limited to a certain cell type or cancer type.

A chemotherapeutic agent is a chemical compound useful in the treatment of cancer. Examples of chemotherapeutic agents include cytostatic agents, cytotoxic agents, growth inhibitory agents and toxins. Exemplary chemotherapeutic agents that may be used in tumour therapy with the proteins of the invention include cyclophosphamide (CAS number 50-18-0, also known as cyclophosphane, and the trade names Endoxan, Neosar, Procytox and Revimmune), AQ4N (1,4-bis-{[2-(dimethylamino-N-oxide)ethyl]amino}5,8-dihydroxyanthracene-9,10-dione, also known as Banoxantrone), ifosfamide (CAS number 3778-73-2), bezyloxyresorufine, 7-Ethoxy-4-trifluoro-methyl-Coumarin (EFC), Bupropion, thiotepa (N,N'N'-triethylenethiophosphoramide, CAS number 52-24-4), mytomycin C (CAS number 50-0-07) and tirapazamine (SR-4233, CAS number 27314-97-2).

In preferred embodiments, the chemotherapeutic agent is a prodrug, or is administered in prodrug form. A prodrug is an inactive form of an drug which is converted to its active form by enzymatic action. The prodrugs for use in the present invention are preferably activated by CYP2B6 and/or NADPH-cytochrome P450 reductase.

Enzyme prodrug therapy may conceivably be applied to conditions other than cancer which are treated with drugs which require enzymatic activation. For example, CYP2B6 metabolises many other drugs in addition to chemotherapeutic drugs. CYP2B6 and the proteins and fusion proteins of the invention may thus be used in prodrug therapy of conditions treatable with such drugs. These drugs include bupriopone, used to help give up smoking and nicotine addiction; clopidogrel, used to prevent and treat atherothrombosis; efavirenz and nevirapine, antiretrovirals used to treat HIV infection and AIDS.

Protein and Nucleic Acid Sequences

The invention provides proteins having the sequences disclosed in any of SEQ ID Nos 1 to 4, variants and fragments thereof, and nucleic acids encoding said sequences. Reference herein to 'proteins' or 'the proteins of the invention' may be understood to encompass said variants and fragments in addition to the sequences disclosed in FIGS. 1-4.

The invention relates in part to provides mutant forms of cytochrome P450 2B6 (CYP2B6). The amino acid sequence of the wild-type human CYP2B6 is shown in FIG. 5 (SEQ ID No 5). The inventors have produced a novel mutant human CYP2B6 protein which has an affinity for CPA 8 times greater than that of the wild-type enzyme, while retaining the same $V_{max}$, by introducing the substitutions I114V, L199M and V477W as shown in FIG. 1 (SEQ ID No 1). The mutant sequence is shown in FIG. 1 (SEQ ID No 1).

As described below, variants and fragments of the amino acid sequence shown FIG. 1 (SEQ ID No 1) are encompassed within the scope of the invention. However, all of the CYP2B6 proteins, variants and fragments of the invention as disclosed herein retain Val at the position corresponding to residue 114 of the amino acid sequence shown FIG. 1 (SEQ ID No 1), Met at the position corresponding to residue 199 of the amino acid sequence shown FIG. 1 (SEQ ID No 1), and Trp at the position corresponding to residue 477 of the amino acid sequence shown FIG. 1 (SEQ ID No 1).

The amino acid sequence of wild-type NADPH-cytochrome P450 reductase is shown in FIG. 2 (SEQ ID No 2). NADPH-cytochrome P450 reductase proteins which are variants and fragments of the amino acid sequence of FIG. 2 (SEQ ID No 2), es described below, are also encompassed within the scope of the invention.

Variant proteins may be naturally occurring variants, such as splice variants, alleles and isoforms, or they may be produced by recombinant means. Variations in amino acid sequence may be introduced by substitution, deletion or insertion of one or more codons into the nucleic acid sequence encoding the protein that results in a change in the amino acid sequence of the protein. Optionally the variation is by substitution of 1, 2, 3, 4, 5, 6, 7, 8, 9, 10, 11, 12, 13, 14, 15, 16, 17, 18, 19, 20 or more amino acids with any other amino acid in the protein. Additionally or alternatively, the variation may be by addition or deletion of 1, 2, 3, 4, 5, 6, 7, 8, 9, 10, 11, 12, 13, 14, 15, 16, 17, 18, 19, 20 or more amino acids within the protein.

Amino acid substitutions may be conservative or non-conservative. Preferably, substitutions are conservative substitutions, in which one amino acid is substituted for another amino acid with similar structural and/or chemical properties. Exemplary conservative substitutions are listed below.

Ala (A) val; leu; ile
Arg (R) lys; gin; asn
Asn (N) gln; his; lys
Asp (D) glu
Cys (C) ser
Gln (Q) asn
Glu (E) asp
Gly (G) pro; ala
His (H) asn; Gln; lys; arg
He (I) leu; val; met; ala
norleucine leu
Leu (L) norleucine; ile; met; ala; phe
Lys (K) arg; Gln; asn
Met (M) leu; phe; ile
Phe (F) leu; val; ile; ala; tyr
Pro (P) ala
Ser (S) thr
Thr (T) ser
Trp (W) tyr; phe
Tyr (Y) trp; phe; thr; ser
Val (V) ile; leu; met; phe; ala; norleucine Variant proteins may include proteins that have at least about 80% amino acid sequence identity with a polypeptide sequence disclosed herein. Preferably, a variant protein will have at least about 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a full-length polypeptide sequence or a fragment of a polypeptide sequence as disclosed herein. Amino acid sequence identity is defined as the percentage of amino acid residues in the variant sequence that are identical with the amino acid residues in the reference sequence, after aligning the sequences and introducing gaps, if necessary, to achieve the maximum percent sequence identity, and not considering any conservative substitutions as part of the sequence identity. Sequence identity may be determined over the full length of the variant sequence, the full length of the reference sequence, or both. Methods for sequence alignment and determination of sequence identity are well known in the art, for example using publicly available computer software such as BioPerl, BLAST, BLAST-2, CS-BLAST, FASTA, ALIGN, ALIGN-2, LALIGN, Jaligner, matcher or Megalign (DNASTAR) software and alignment algorithms such as the Needleman-Wunsch and Smith-Waterman algorithms.

Fragments of the proteins and variant proteins disclosed herein are also encompassed by the invention. Such fragments may be truncated at the N-terminus or C-terminus, or may lack internal residues, for example, when compared with a full length protein. Certain fragments lack amino acid residues that are not essential for enzymatic activity. Preferably, said fragments are at least about 10, 20, 30, 40, 50, 60, 70, 80, 90, 100, 110, 120, 150, 250, 300, 350, 400, 450, 500 or more amino acids in length.

Preferred fragments of the proteins disclosed herein comprise all or a part of the active site. Preferred fragments of CYP2B6 comprise or consist of amino acids 1-490 of the full length sequence shown in FIG. 1 (SEQ ID No 1). Preferred fragments of NADPH-cytochrome P450 reductase comprise or consist of fragments comprising or consisting of amino acids 27-678 of the amino acids sequence shown in FIG. 2 (SEQ ID No 2).

The variants and fragments of the invention preferably retain a biological activity of the full-length protein disclosed herein. Variants and fragments of full-length CYP2B6 preferably have the activity of oxidising a substrate such as cyclophosphamide, or other substrate as disclosed herein, in particular by catalysing hydroxylation of 4-OH-CPA. In a preferred embodiment, said variants and fragments have an affinity for CPA greater than that of the wild-type CYP2B6 sequence shown in FIG. 5, preferably at least 2, 3, 4, 5, 6, 7, 8, 9 or 10 times that of the wild-type sequence. In a particularly preferred embodiment, said variants and fragments have an affinity for CPA the same as, substantially the same as, or greater than, that of the full-length mutant CYP2B6 sequence shown in FIG. 1 (SEQ ID No 1). Methods for assaying said activity and affinity are described below and in Nguyen et al, Mol Pharmacol 2008, 73: 1122-1133. Variants and fragments of NADPH-cytochrome P450 reductase preferably have the activity of reduction of cytochrome c, preferably in a NADPH-dependent fashion. In a preferred embodiment, said variants and fragments have an activity the same as, substantially the same as, or greater than, that of the full-length mutant NADPH-cytochrome P450 reductase sequence shown in FIG. 2 (SEQ ID No 2). Methods for assaying said activity are described below and in Yasukochi et al; Arch Biochem Biophys 1980, 202: 491-498.

The skilled person will be able to determine amino acid residues which may be inserted, substituted or deleted without adversely affecting the activity of the protein using knowledge of the protein structure available in the art and publicly available molecular modelling techniques (see for example Nguyen et al, Mol Pharmacol 2008, 73: 1122-1133). The variation allowed may be determined by systematically making insertions, deletions or substitutions of amino acids in the sequence and testing the resulting variants for activity exhibited by the parent protein.

Vectors

Nucleic acids encoding the proteins of the invention may be incorporated into vectors, for example replicable vectors for cloning and amplification, vectors for transfection or infection of cells, or vectors for in vitro production of the proteins. All such vectors are included within the scope of the invention.

The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Many vectors are publicly available and construction of suitable vectors employs standard ligation techniques which are known to the person skilled in the art.

Where the vector is intended to introduction of the protein into the cells of a patient, viral vectors are preferred, although the vector may be any DNA or RNA vector used or suitable to VDEPT or GDEPT therapies. Viral vectors may include DNA viruses such as adenovirus and retroviruses, preferably retroviruses which preferentially infect dividing cells such as tumour cells. Exemplary retroviruses include lentivirus, alpharetrovirus, betaretrovirus, gammaretrovirus, deltaretrovirus and epsilonretrovirus. Retroviral shuttle vectors are also encompassed within the scope of the invention. Retroviral shuttle vectors are generated using the DNA form of the retrovirus contained in a plasmid with the certain parental endogenous retroviral genes (e.g. gag pol and env) removed and the DNA sequence of interest inserted. Retroviral shuttle vectors may be derived from retroviruses or from certain DNA viruses, such as the BPV virus or adenoviruses.

The vector may be an expression vector suitable for expression of the protein, for example in a cell in culture, or within a tumour cell in a patient. The nucleic acid encoding the protein of the invention will preferably be operably linked to a promoter permitting expression of the protein. 'Operably linked' means joined as part of the same nucleic acid molecule, suitably positioned and oriented for transcription to be initiated from the promoter. Thus there may be elements such as 5' non-coding sequence between the promoter and coding sequence which is not native to either the promoter nor the coding sequence. Such sequences can be included in the vector if they do not impair the correct control of the coding sequence by the promoter.

Suitable promoters include viral promoters such as mammalian retrovirus or DNA virus promoters, for example MLV, CMV, RSV and adenovirus promoters. Preferred adenovirus promoters are early gene promoters. Strong mammmalian promoters may also be suitable. Variants of such promoters retaining substantially similar transcriptional activities may also be used.

Fusion Proteins

Fusion proteins are chimeric proteins created by joining two or more genes encoding separate proteins or protein fragments, such as different protein domains, into a single reading frame encoding a single translated protein. The fusion proteins of the present invention preferably comprise a CYP2B6 protein as disclosed herein, and a NADPH-cytochrome P450 reductase protein as disclosed herein. In a preferred embodiment, said fusion protein comprises residues 1-490 of CYP2B6 and residues 57-678 of NADPH-cytochrome P450 reductase, though any of the full-length proteins, variants and fragments disclosed herein may be used. The CYP2B6 protein may be upstream or downstream of the NADPH-cytochrome P450 reductase. Preferably, the CYP2B6 protein is upstream of the NADPH-cytochrome P450 reductase.

When context permits, reference herein to 'the proteins of the invention', 'the proteins disclosed herein' etc should be understood to encompass said fusion proteins.

The proteins or protein fragments making up the fusion protein may be separated by a linker peptide sequence or spacer. The linker serves to separate the component proteins or protein fragments and aid effective folding and activity of the individual components. The linker may comprise an enzyme cleavage site to permit the component polypeptides to be separates by enzymatic digestion. The linker may be, for example, 1, 2, 3, 4, 5, 6, 7, 8, 9, 10, 11, 12, 13, 14, 15 amino acids or more in length. Preferably, the linker is less than 10, less than 8, less than 7, less than 6 or less than 5 amino acids in length. Exemplary linkers for use in the fusion proteins of the present invention comprise $Ser_n Thr$, where 'n' is any whole integer, preferably 1, 2, 3, 4, 5, 6, 7, 8, or 9. In a preferred embodiment, 'n' is 5. In another preferred embodiment, 'n' is 3.

Methods of Treatment

'Treatment' includes both therapeutic treatment and prophylactic or preventative treatment, wherein the object is to prevent or slow down the targeted pathologic condition or disorder. Those in need of treatment include those already with the disorder as well as those prone to have the disorder or those in whom the disorder is to be prevented. The terms 'therapy', 'therapeutic', 'treatment' or 'treating' include reducing, alleviating or inhibiting or eliminating the symptoms or progress of a disease, as well as treatment intended to reduce, alleviate, inhibit or eliminate said symptoms or progress. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, methods and compositions of the invention are used to delay development of a disease or disorder or to slow the progression of a disease or disorder.

Treatment in accordance with the invention includes a method of treating a cancer or other neoplastic disorder which comprises administering to a patient in need of treatment a protein, vector or pharmaceutical composition of the invention. Preferably, the treatment further comprises administering to said patient a chemotherapeutic drug, preferably a drug in prodrug form. The two components may be administered together, for example in the form of a combined pill, or separately. Administration may be sequential or simultaneous. 'Sequential' administration indicates that the components are administered at different times or time points, which may nonetheless be opverlapping. Simultaneous administration indicates that the components are administered at the same time.

Preferably, an effective amount, preferably a therapeutically effective amount of the protein or vector of the invention is administered. An 'effective amount' refers to an amount effective, at dosages and for periods of time necessary, to achieve the desired therapeutic or prophylactic result. The effective amount may vary according to the drug or prodrug with which the protein or vector is co-administered.

A 'therapeutically effective amount' of a protein or vector of the invention may vary according to factors such as the disease state, age, sex, and weight of the individual, and the ability of the protein, to elicit a desired therapeutic result. A therapeutically effective amount encompasses an amount in which any toxic or detrimental effects of the protein are outweighed by the therapeutically beneficial effects. A therapeutically effective amount also encompasses an amount sufficient to confer benefit, e.g., clinical benefit.

In the case of pre-cancerous, benign, early or late-stage tumors, the therapeutically effective amount of the composition of the invention may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit or delay, to some extent, tumor growth or tumor progression; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

'Neoplastic disease', cancer' and 'tumour' refer to or describe the physiological condition in mammals that is typically characterized by unregulated cell growth. Examples of cancer include carcinoma, lymphoma, blastoma, sarcoma, and leukemia or lymphoid malignancies. More particular examples of such cancers include squamous cell cancer, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, gliosarcoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma; chronic lymphocytic leukaemia (CLL); acute lymphoblastic leukaemia (ALL); hairy cell leukaemia; chronic myeloblastic leukaemia; head and neck cancer; and associated metastases. In certain embodiments, cancers that are amenable to treatment by the antibodies of the invention include cancers of the head and neck, leukaemia, lymphoma, gliosarcoma, pancreatic cancer, breast cancer and melanoma.

Pharmaceutical Compositions and Administration

The proteins and vectors of the invention may be formulated in a pharmaceutical composition in combination with a carrier. Carriers include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG).

The formulation or pharmaceutical compositions of the invention may also contain more than one active compound. For example, it may comprise a chemotherapeutic agent or prodrug in addition to the protein or vector of the invention. Other molecules or compounds with complementary activities, such as immunosuppressive agents, may also be included.

The proteins, vectors and compositions of the invention may be administered via any route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy.

The invention will now be described in more detail with reference to the following figures and examples.

All documents cited herein are hereby incorporated by reference in their entirety.

FIGURES

FIG. 1 shows the amino acid sequence of a mutant CYP2B6 comprising 114V, 199M and 477W.

FIG. 2 shows the amino acid sequence of wild-type human NAPDH-cytochrome P450 reductase.

FIG. 3 shows the sequence of the mutant CYP2B6-NAPDH-cytochrome P450 reductase fusion protein.

FIG. 4 shows the sequence of wild-type human CYP2B6 protein.

Figure 9:
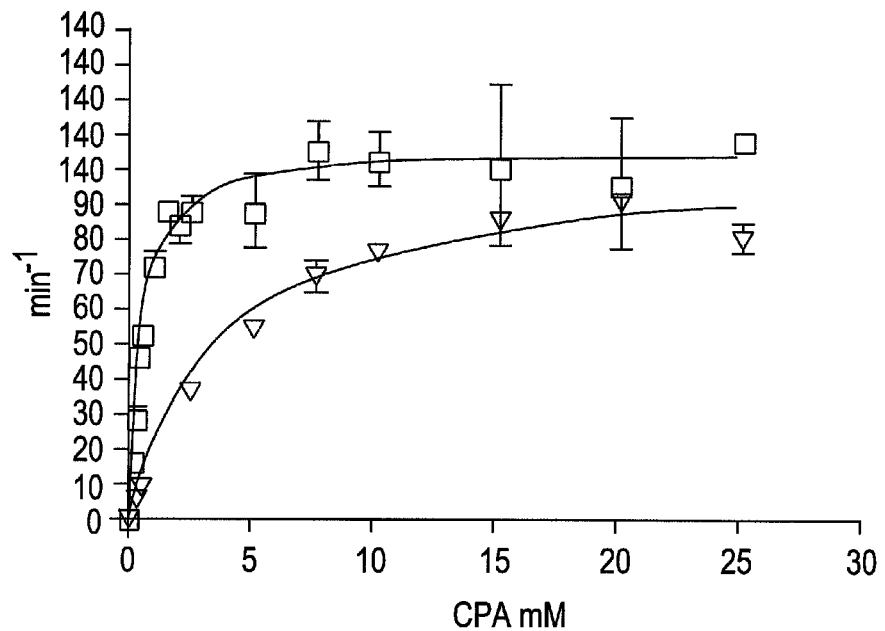

FIG. 9 shows $V_{max}$ and $K_m$ of CPA-4' hydroxylation in yeast microsomes expressing CYP2B6 wt (filled inverted triangles) and CYP2B6TM (triple mutant, filled squares). The $V_{max}$ of the wild-type protein was 107.3±3.74 min$^{-1}$ and the $K_m$ was 4.33±0.5 mM. The $V_{max}$ of the triple mutant was 107.5±3.4 min$^{-1}$ and the $K_m$ was 0.51±0.08 mM. CYP2B6TM showed a 8.5 increase in CPA-40H catalytic efficiency ($V_{max}/K_m$), mainly as a result of an increase in enzyme affinity.

Figure 10:
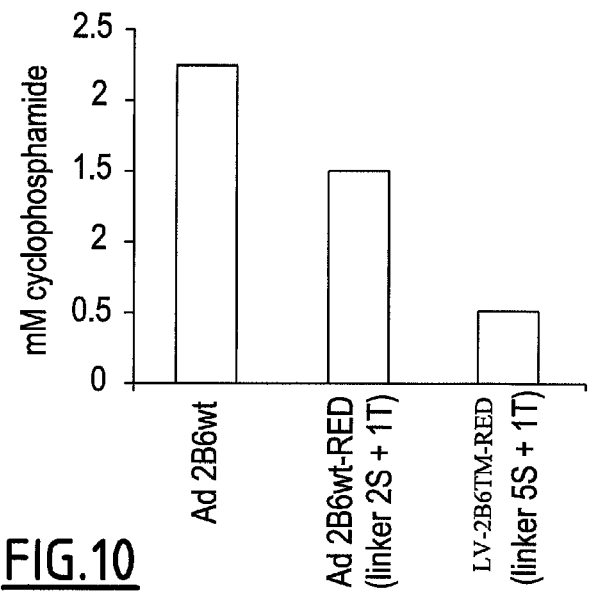

FIG. 10 shows $IC_{50}$ values of infected A549 pulmonary cell lines after CPA treatment. A549 cells were infected with Ad-CYP2B6 wt (200MOI), Ad-CYP2B6 wt-RED (linker 2S+1T) (200 MOI) and treated with CPA for five days from the day following infection, or infected by LV-CYP2B6TM-RED (linker 5S+1T) (100MOI) and treated for five days. Cells expressing CYP2B6TM-RED were more sensitive to CPA than cells expressing CYP2B6 wt or CYP2B6 wt-RED.

Figure 11:
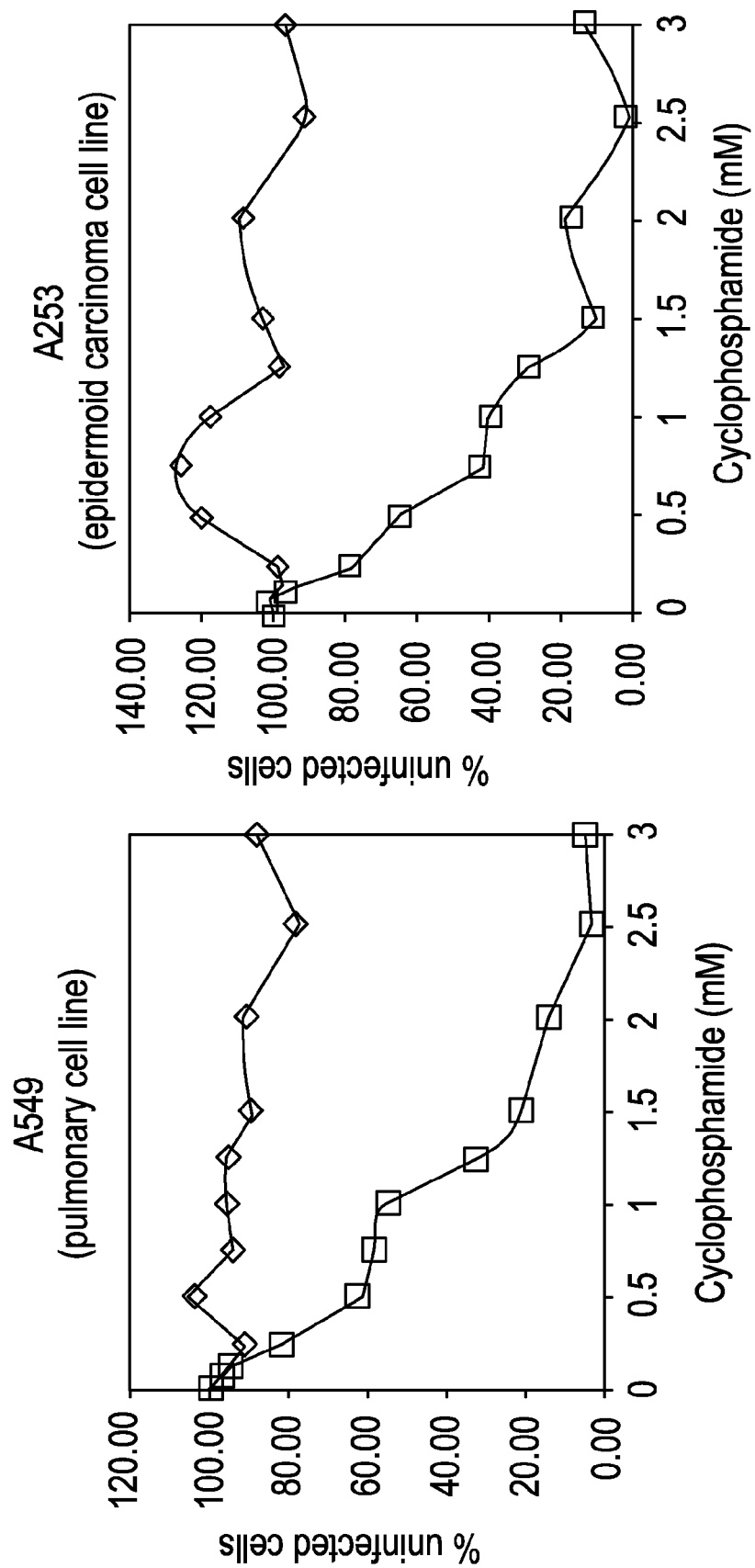

FIG. 11 shows the cytotoxicity of cyclophosphamide on human tumour cell lines A549 (pulmonary cancer cell line) and A253 (submandibular gland carcinoma) expressing GFP (control; filled diamonds) or CYP2B6TM-RED (linker 5S+1T; filled squares) after 2 days of treatment.

Figure 12:
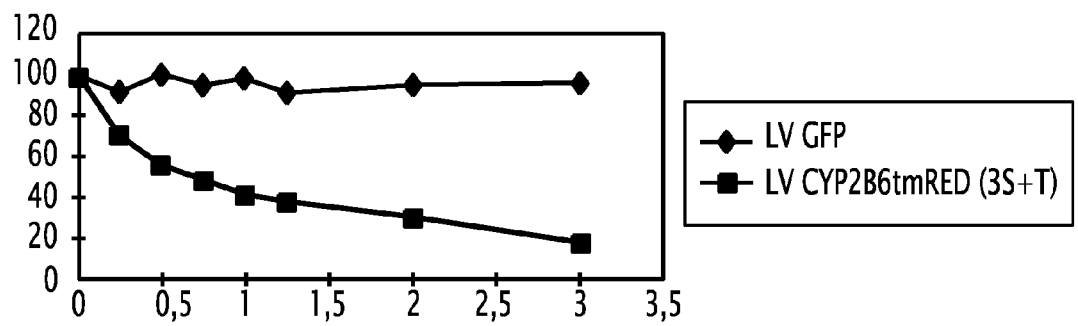

FIG. 12 shows the cytotoxicity of cyclophosphamide on TC1-Luc2 cells expressing GFP (control; filled diamonds) or CYP2B6TM-RED (linker 5S+1T; filled squares) in 96-well plates after 2 days of treatment.

Figure 13:
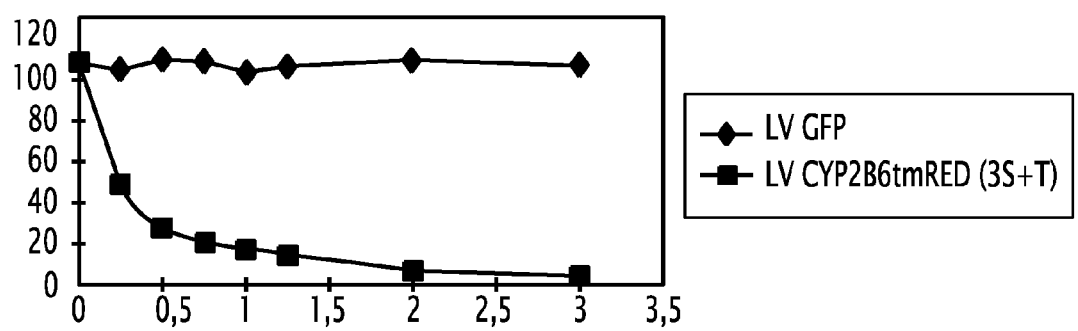

FIG. 13 shows the cytotoxicity of cyclophosphamide on TC1-Luc2 cells expressing GFP (control; filled diamonds) or CYP2B6TM-RED (linker 5S+1T; filled squares) in 96-well plates after 3 days of treatment.

Figure 14:
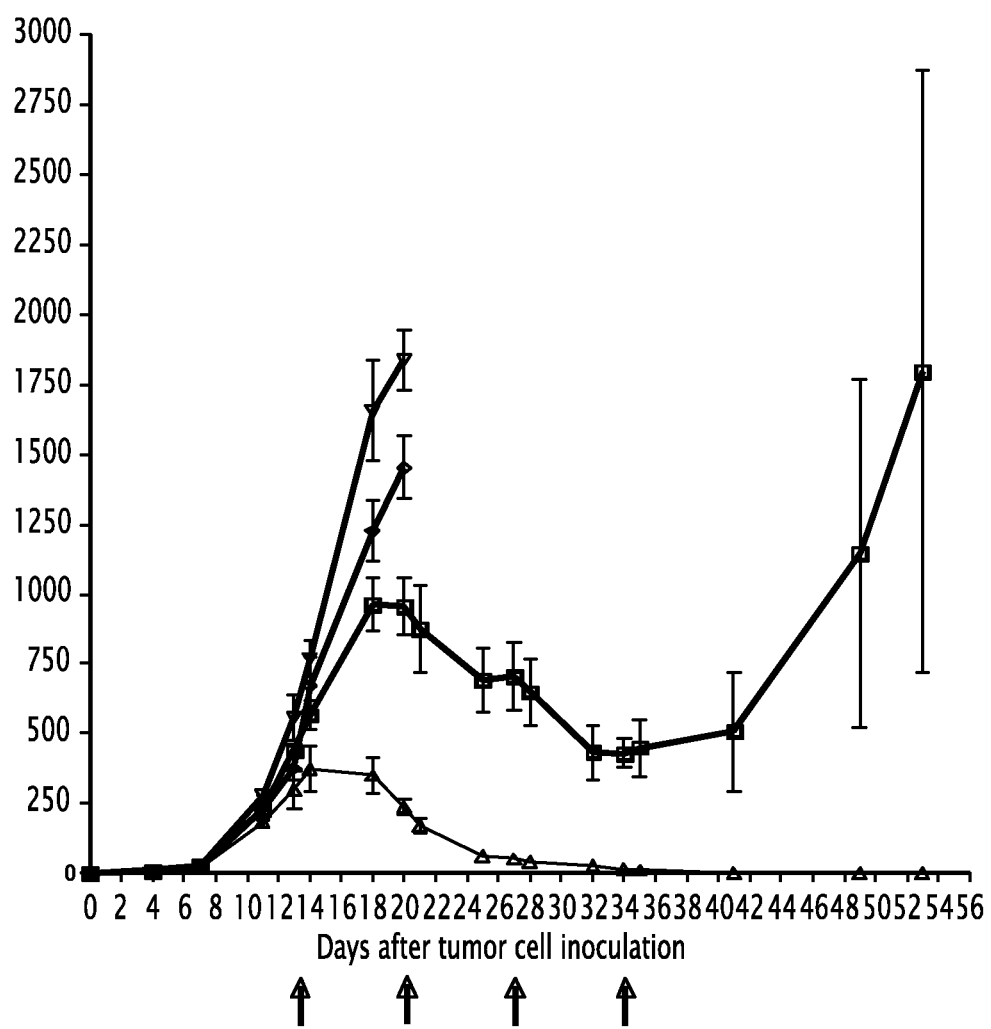

FIG. 14 shows change in tumour volume after treatment with CPA in lung tumour explants in a mouse model. C57 B116 mice were subcutaneously injected with TC1 cells expressing CYP2B6TM-RED or with uninfected cells. CPA was administered at 140 mg/kg by i.p. injection (arrows). In control mice untreated with CPA, tumour volume increased rapidly in both uninfected cells (inverted triangles) and in CYP2B6TM-RED-expressing cells (diamonds). CPA treatment slowed this rapid increase in uninfected tumour cells but obtained no reduction in overall tumour size (squares). In contrast, CPA treatment produced a rapid regression of tumours expressing CYP2B6TM-RED (triangles).

EXAMPLES

Construction of the CYP2B6 Triple Mutant (CYP2B6TM):
Site-directed mutagenesis was based on the QuikChange kit (Stratagene, Amsterdam, The Netherlands) using mutagenic primers and V-60CYP2B6 wt (described in Gervot L, Rochat B, Gautier J C, Bohnenstengel F, Kroemer H, de Berardinis V, et al (1999): Human CYP2B6: expression, inducibility and catalytic activities. Pharmacogenetics 9:295-306) as template followed by DpnI digestion and transformation into competent DH5a bacteria. Three mutations were made: I114V, L199M and V477W. The CYP2B6 triple mutant was sequenced to be sure that the desired mutation was obtained.

Construction and Expression of the CYP2B6 Triple Mutant-Reductase (CYP2B6TM-RED) Fusion Genes with Different Linkers.

To have a complete system that can operate efficiently in the tumoral cells, the inventors chose to express NADPH-P450 reductase (RED) as part of a fusion protein with CYP2B6 instead of two separate proteins. The fusion gene was constructed with two sequences of human origin: human CYP2B6, at the N-terminus, bound to the soluble portion of human NADPH-CYP reductase, at the C-terminus. The amino-terminal hydrophobic region of the RED (first 56 amino acids) was deleted and the fusion protein was anchored to the membrane by the CYP2B6 N-terminal. The amino-terminal hydrophobic region of CYP2B6 was important for correct localisation of the newly synthesized polypeptide into the microsomal membranes as well as for its sufficient enzymatic activity. The remaining hydrophilic C-terminal of RED (from Ile-57 to stop codon-678) contains the FMN-binding domain, the connecting domain and the FAD-NADPH-binding domains (Wang et al, PNAS 94:8411-8416, 1997) allowing efficient electron transfer.

The inventors had previously reported the successful construction and expression in mammalian cells of an active human CYP2B6-human NADPH P450 reductase in mammalian cells using a Ser-Ser-Thr linker. (Tychopoulos et al, Cancer Gene Ther 2005, 12: 497-508). However, although our fusion protein was functional and therefore that electrons were successfully transferred from the flavin moiety to the heme in the CYP2B6 fragment of the protein, this electron transfer was nevertheless not optimal. The structure of the hinge region between CYP2B6 and RED domains had to be optimized.

From an investigation of linker peptides joining domains in 51 natural protein tertiary structures, Argos (J. Mol. Biol, 211: 943-958, 1990) showed that Thr, Ser, Gly are desirable linker constituents. The preferred linker amino acids are mostly small and not hydrophobic, the basic and acidic groups are excluded, as well as large and bulky hydrophobic residues and the average length of the linker is 6.5 residues. Moreover, a peptide linker used to connect two polypeptide domains and comprising a large proportion of serine residues produces a fusion protein with an improved resistance to proteolysis.

The inventors compared the effect of several linkers on the efficiency of the CYP2B6-human NADPH P450 reductase fusion protein to metabolize CYP2B6 substrates, such as cyclophosphamide or benzyloxyresorufin. The linkers tested were: Ser-Thr, Ser-Ser, Ser-Ser-Thr and $(Ser)_{3-7}$-Thr.

Figure 6:
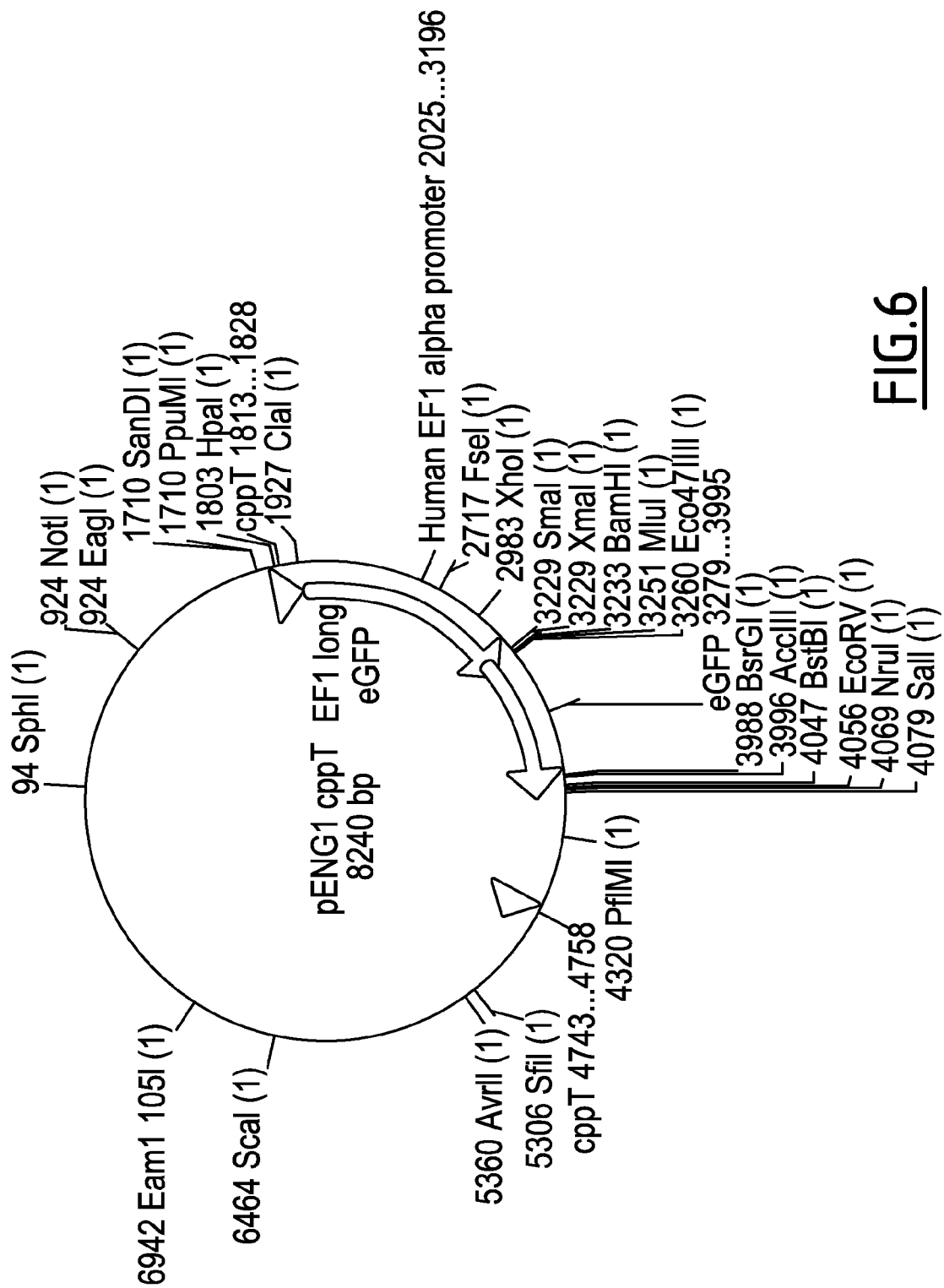
FIG. 6 shows plasmid pENG1 delta cppT (pENG1 cppT.EF1 long eGFP deleted of eGFP by excision of the fragment between Eco47III and BsrG1 restriction sites).
Figure 7:
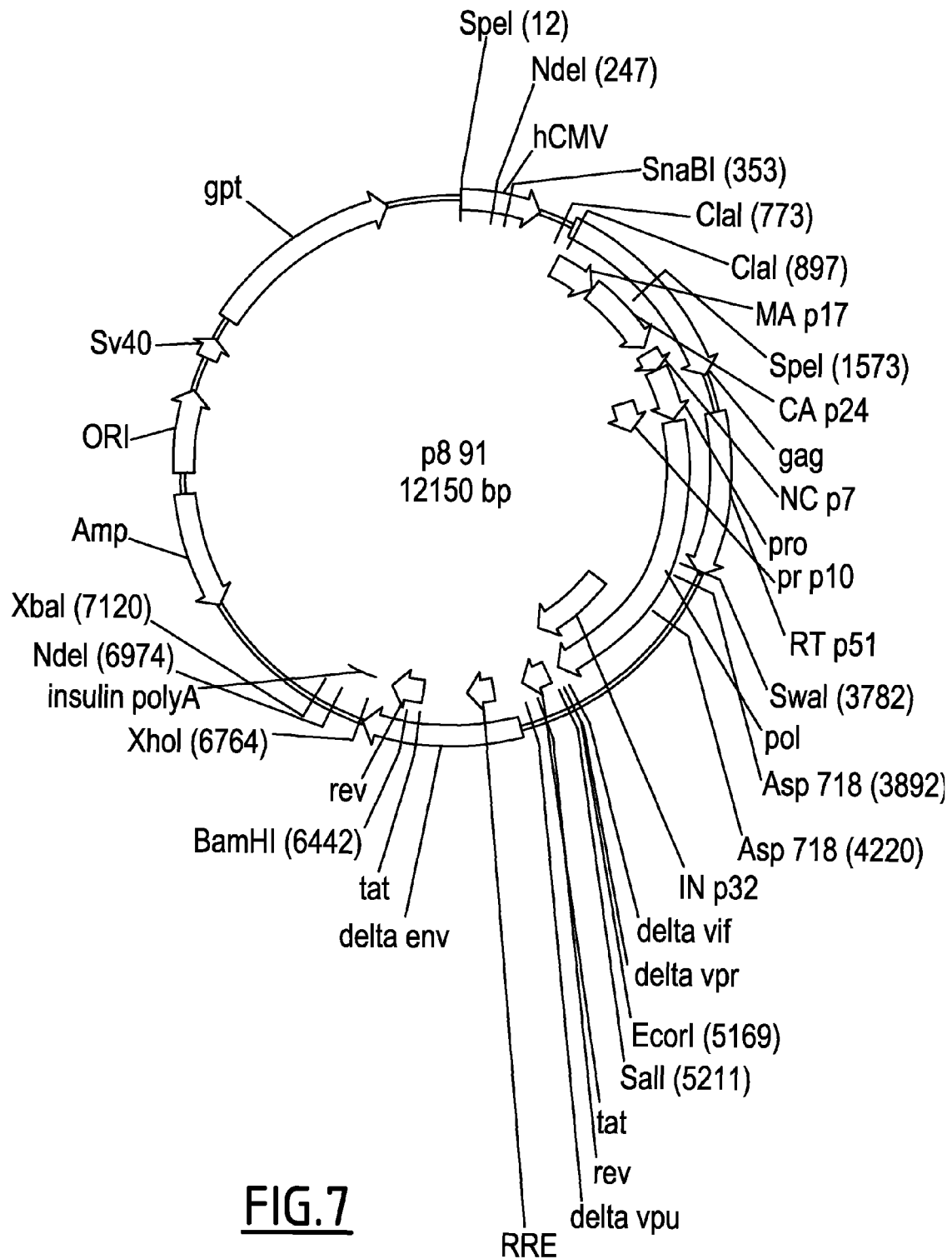
FIG. 7 shows plasmid pCMV8.91 coding for gag and pot proteins.

CYP2B6TM (the whole coding sequence without the stop codon TGA) and the soluble part of human RED (from by 171 until the stop codon TAG) with different linker sequences (1ser+1thr, 2ser or 2 to 7ser+thr) between the two proteins (FIG. 6) was subcloned into pYEDP60 plasmid and expressed in W(R) S. Cerevisiae yeast strain to test its efficiency to metabolize cyclophosphamide or into pENG1 delta cppT (pENG1 cppT.EF1 long eGFP deleted of eGFP by excision of the fragment between Eco47III and BsrG1 restriction sites, FIG. 7) for lentivirus production. The constructs were sequenced using an automatic Perkin Elmer sequencer to ensure that the correct reading frame was retained whatever the linker sequence used.

Expression in Yeasts.

The yeast expression plasmid pYeDP60 and the W(R) S. cerevisiae strain were constructed by substitution of the natural W303-1 B yeast reductase promoter by the galactose inducible GAL10-CYC1 hybrid promoter (described in Truan G, Cullin C, Reisdorf P, Urban P, Pompon D. (1993): Enhanced in vivo monooxygenase activities of mammalian P450s in engineered yeast cells producing high levels of NADPH-P450 reductase and human cytochrome b5. Gene 125:49-55).

CYP2B6 wt or CYP2B6TM alone or in fusion with RED were expressed in the MR) yeast strain, in which yeast NADPH cytochrome P450 reductase was constitutively expressed. The pYeDP60 plasmids were introduced into intact yeast cells based on a refined lithium acetate-mediated protocol as described in Truan et al, 1993, above. Yeast culture conditions were as described in Bellamine A, Gautier J C, Urban P, Pompon D (1994): Chimeras of the human cytochrome P450 1A family produced in yeast. Accumulation in microsomal membranes, enzyme kinetics and stability. Eur J Biochem 225:1005-13.

Cell Lines

Human pulmonary cell line (A549) was cultured in RPMI containing 10% fetal bovine serum (FBS) and supplemented with penicillin (200 U/ml), streptomycin (50 µ/ml) and fungizone (0.5 µ/ml).

Human A-253 head and neck epidermoid carcinoma cell line was grown as a monolayer in Dulbecco's modified Eagle's medium supplemented with 10% fetal bovine serum, nonessential aminoacids for Dulbecco's modified Eagle's medium, penicillin at 200 U/ml, streptomycin at 50 µ/ml and fungizone (0.5 µ/ml).

Adenoviral Infections

CYP2B6 wt or CYP2B6 wt-RED were cloned into serotype 5 adenovirus. The recombinant adenoviral vectors were generated by homologous recombination between a shuttle vector (pTrack-CMV) and the adenoviral backbone vector (pAdEASY-1) (see He T C, Zhou S, da Costa L T, Yu J, Kinzler K W, Vogelstein B. (1998): A simplified system for generating recombinant adenoviruses. Proc Natl Acad Sci USA 95:2509-14). The deletion of the adenoviral E1 renders the virus unable to produce infectious viral particles in target cells, and deletion of the E3 region is dispensable for viral production since it encodes proteins involved in evading host immunity. An adenoviral vector expressing LacZ was used as control (Ad-LacZ).

The standard infection procedure consisted in diluting the desired adenoviral quantity into cell culture medium (with 2% FBS) to infect cells with 200 multiplicity of infection (MOI) (i.e., number of infectious particles/cell). Cells were incubated for 4 hours with the adenoviral constructs and then reconstituted in cell culture medium.

Lentiviral Infections

Figure 8:
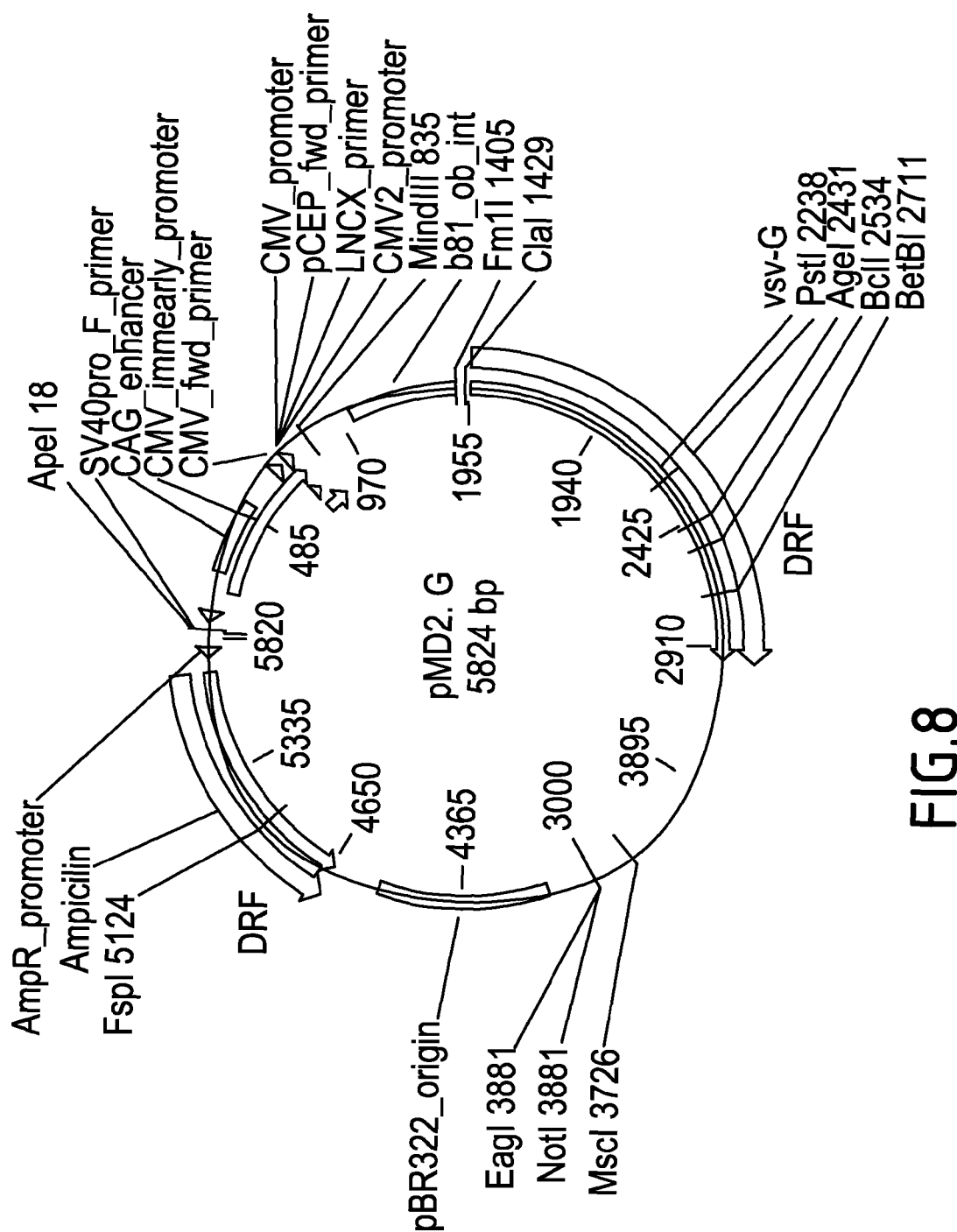
FIG. 8 shows plasmid p.MD2G coding for envelope proteins.

Lentiviral production was performed in HEK293T cells transfected with 3 plasmids: pENG1 delta cppT-CYP2B6TM-RED, pCMV8.91 coding for gag and pol proteins (FIG. 7) and p.MD2G coding for envelope proteins (FIG. 8). Quantification of viral particles was estimated by p24 measurement (HIV-1 p24 antigen ELISA, Zeptometrix corporation). A lentiviral vector expressing green fluorescent protein (GFP) was used as control (LV-GFP).

The standard infection procedure consisted in diluting the desired lentiviral quantity into cell culture medium to infect cells with 100 MOI. To increase lentivirus infection protamine sulfate (8 µ/ml) was added to the medium. Cells were incubated 3 hours in a minimal volume before adding cell culture medium to recommended volume. 24 hours later, the cell culture medium was renewed.

Transgene Expression

Transgene expression was checked by Western blot using a polyclonal anti-CYP2B6 antibody and/or a polyclonal anti-human RED antibody (Lifespan Biosciences). After adenoviral infection, overexpression of the transgenes was maximal at 3 days after infection, as previously described (Narjoz C, Marisa L, Imbeaud S, Paris A, Delacroix H, Beaune P, et al. Genomic consequences of cytochrome P450 2C9 overexpression in human hepatoma cells. Chem Res Toxicol 2009; 22:779-87). After lentiviral infection, overexpression of the transgenes remained stable from 8 days after infection until several weeks since the transgene was integrated in the cell genome. These results were confirmed by immunofluorescence.

Microsomal Preparation

Yeast microsomes were prepared based on the mechanical disruption method using glass beads as described in Bellamine A, Gautier J C, Urban P, Pompon D. (1994): Chimeras of the human cytochrome P450 1A family produced in yeast. Accumulation in microsomal membranes, enzyme kinetics and stability. Eur J Biochem 225:1005-13.

Three days after adenoviral infections or at least 8 days after lentiviral infection, infected cells were trypsinized and washed twice with phosphate-buffered saline (PBS), and the cellular pellet was resuspended in STE buffer (0.25 mM Sucrose, 10 mM Tris, 1 mM EDTA pH 7.4) containing anti-proteases (Roche diagnostics GmbH, Germany) and sonicated three times 10 seconds. The sonicated lysate was centrifuged at 9000 g for 20 minutes, and subsequently the supernatant was centrifuged at 100,000 g for 1 hour. The 100,000 g pellet containing the microsomes was resuspended in buffer (100 mM NaPO4, 10 mM MgCl2, 20% Glycerol (w/v) at pH 7.4), aliquoted and frozen at −80° C.

Microsomal protein concentration was determined by the bicinchoninic acid (BCA) procedure according to the manufacturer's instructions (Pierce, Rockford, Ill.) using bovine serum albumin as a standard CPA 4-Hydroxylase Activity.

The fluorometric determination of yeast microsomal CPA 4-hydroxylase was adapted from a technique described previously (Roy P, Yu L J, Crespi C L, Waxman D J. (1999): Development of a substrate-activity based approach to identify the major human liver P-450 catalysts of cyclophosphamide and ifosfamide activation based on cDNA-expressed activities and liver microsomal P-450 profiles. Drug Metab Dispos 27:655-66) for a 96-well microplate with several modifications. Incubations were carried out for 1 h at 28° C. in a total volume of 200 µl and included 100 mM sodium phosphate buffer, pH 7.4, 1 mM EDTA, 10 pmol of CYP2B6 wt or CYP2B6TM or CYP2B6TM-RED with different linkers (microsomal P450 content was spectrally determined by the method of Schoene B, Fleischmann R A, Remmer H, von Oldershausen H F. (1972): Determination of drug metabolizing enzymes in needle biopsies of human liver. Eur J Clin Pharmacol 4:65-73) and 10 mM CPA. Reactions were initiated by adding the NADPH-generating system and stopped by the addition of 200 µl of 10% trichloroacetic acid. After centrifugation at 13,000 g and 4° C. for 15 min to pellet the proteins, 300 µl of the supernatant was transferred to a clean test tube containing 160 µl of the fluorescence mixture (6 mg of 3-aminophenol and 6 mg of hydroxylamine hydrochloride freshly dissolved in 1 ml of 1N HCl). Samples were heated at 90° C. for 20 min to form 7-hydroxyquinoline by condensation of the 4-hydroxy-CPA with 3-aminophenol. After cooling to room temperature, fluorescence reading were performed on a Bio-tek FL600 microplate fluorescence reader (excitation at 350 nm and emission at 515 nm). Under these assay conditions, product formation was linear with time, and the enzyme concentration and amount of 4-hydroxy-CPA under these assay conditions was determined based on a standard curve of 4-hydroxy-CPA (0-20 µM) incubated with bovine serum albumin and treated in parallel under the same assay conditions.

The kinetic constants of cyclophosphamide hydroxylase were determined by a nonlinear regression with 15 substrate concentrations (0.05 to 25 mM). Data were analyzed using Prism software (Graph-Pad Software, Inc., San Diego, Calif.) to calculate kinetic parameters ($K_m$, $V_{max}$), with $V_{max}$ values expressed as moles of product formed per minute, normalized to the moles of P450 included in each reaction (turnover number expressed as minutes$^{-1}$). Data shown were based on duplicate determinations for each data point.

$V_{max}$ and $K_m$ of CPA-4' hydroxylation were determined in yeast microsomes expressing CYP2B6 wt and CYP2B6TM (FIG. 9). CYP2B6TM showed a 8.5 increase in CPA-4OH catalytic efficiency ($V_{max}/K_m$), mainly as a result of an increase in enzyme affinity.

RED Activity Assay

RED activity was measured in the cellular microsomal fraction. The NADPH-dependent reduction of cytochrome c by RED was assayed as described in Yasukochi Y, Okita R T, Masters B S. (1980): Comparison of the properties of detergent-solubilized NADPH-cytochrome P-450 reductases from pig liver and kidney. Immunochemical, kinetic, and reconstitutive properties. Arch Biochem Biophys 202:491-8. Cytochrome c was added at a final saturating concentration of 80 M and RED activity was calculated as nmol cytochrome c reduced/mn/mg using=21 mM$^{-1}$ cm$^{-1}$ at 550 nm Vmax, Km and Vmax/Km were determined in yeast microsomes expressing CYP2B6 wt, CYP2B6TM and CYP2B6TM-RED with different linkers (Table 1). For all fusion proteins, CPA-4OH catalytic efficiency was in the same range of magnitude, with weak variations according to the size of the linker used, and comparable to that observed with CYP2B6TM alone, showing that addition of RED did not affect CYP2B6TM catalytic efficiency. On the other hand, after deduction of endogenous yeast reductase activity, reductase activity due to fusion protein expression differed according to linker size from 721 to 6528 nmol/min/mg. From these results, three CYP2B6TM-RED constructions with different reductase activities (indicated with asteriks) were used to produce recombinant lentivirus.

TABLE 1

Effect of the linker on CPA hydroxylase activity and NADPH reductase activity of the CYP2B6- RED fusion protein

| Linker (where present) | CPA hydroxylase activity | | | Reductase activity |
|---|---|---|---|---|
| | $V_{max}$ | $K_m$ | $V_{max}/K_m$ | |
| CYP2B6wt (w/o reductase) | 62.5 | 4.9 | 12.7 | [n/a] |
| CYP2B6TM (w/o reductase) | 105.5 | 1.05 | 100.5 | [n/a] |
| 1Ser + 1Thr | 98.82 | 1.31 | 75.4 | 342.0 |
| 2Ser | 87.95 | 1.1 | 80.0 | 72.1 |
| 2Ser + 1Thr | 92.28 | 1.14 | 81 | 344.9 |
| 3Ser + 1Thr | 114.5 | 1.1 | 104.1 | 652.8 |
| 4Ser + 1Thr | 85.22 | 1.11 | 76.8 | 98.6 |
| 5Ser + 1Thr | 108.5 | 0.89 | 141.9 | 291.7 |
| 6Ser + 1Thr | 94.36 | 0.97 | 97.27 | 313.9 |
| 7Ser + 1Thr | 95.11 | 1.04 | 91.45 | 119.8 |

CPA hydroxylase activity $V_{max}$ is expressed as nmol 4OH-CPA/min/nmol CYP2B6 and $K_m$ as µm.
Reductase activity is expressed as nmol/min/mg, adjusted to take account of intrinsic yeast reductase activity.

CPA hydroxylase activity $V_{max}$ is expressed as nmol 4OH-CPA/min/nmol CYP2B6 and $K_m$ as µm. Reductase activity is expressed as nmol/min/mg, adjusted to take account of intrinsic yeast reductase activity.

In-Vitro Cytotoxicity Assays

Cells were infected in six-well plates at 4 10$^5$ cells/well, with adenoviral constructs or lentiviral constructs as previously described. Cells were then trypsinized and seeded into 96-well plates at 10$^4$ cells/well in triplicates. Cells infected with an adenoviral vector expressing LacZ or with a lentiviral vector expressing green fluorescent protein (GFP) were used as controls. Cells were treated with CPA 0-3 mM for 5 days, cell viability was assayed using the "Celltitre 96® AQ$_{ueous}$ One Solution Cell Proliferation Assay" (Promega) according to the manufacturer's instructions. This colorimetric assay measures the dehydrogenase activity in the metabolically active mitochondria of viable cells. After the 5-day CPA treatment, 10 µl of One Solution Reagent (Promega) were added to 100 µl of cell culture medium and cells were incubated for 2 hours at 37° C., and subsequently the plates were read at 490 nm using a 96-well plate reader. Cell viability was expressed as the percentage of viable cells compared to those infected by controls (Ad-LacZ or LV-GFP) treated at identical CPA concentrations.

IC$_{50}$ values of infected A549 pulmonary cell lines after CPA treatment are shown in FIG. 10. Cells expressing CYP2B6TM-RED were more sensitive to CPA than cells expressing CYP2B6 wt or CYP2B6 wt-RED.

Cyclophosphamide cytotoxicity was compared in A549 and A253 cell lines, expressing GFP (control) or CYP2B6TM-RED (linker 5S+1T) as shown in FIG. 11. Expression of the fusion gene rendered these previously CPA-insensitive cell lines sensitive to weak doses of CPA.

Cyclophosphamide cytotoxicity was also compared in TC1-LUC2 A549 and A253 cell lines, expressing GFP (control) or CYP2B6TM-RED (linker 3S+1T) as shown in FIGS. 12 and 13. Expression of the fusion protein also rendered these cell lines sensitive to weak doses of CPA. In 6-well plates, all of the CYP2B6TM-RED-infected cells were dead after treatment with 1.5 or 3 mM CPA. Cells infected with GFP were unaffected. Similar results were seen in 96-well plates, as shown in FIGS. 12 and 13. Infection de cellules TC1-Luc2 par lentivirus recombinants et traitement cyclophosphamide (CPA).

In Vivo Cytotoxicity Assays

To test the capacity of the triple mutant to enhance the response to CPA in vivo, a mouse model was used. Mouse pulmonary tumour cells (TC1-Luc2) were infected with a lentivirus vector carrying the CYP2B6TM-RED construct and injected subcutaneously into C57Bl6 mice. As a control, uninfected TC1 cells-were injected. TC1-Luc2 cells express luciferase, permitting tumour size to be monitored via bioluminescence.

In initial experiments, 10 mice were injected with CYP2B6TM-RED-TC1 cells and 10 were injected with uninfected TC1 cells. Tumour growth was monitored, and when the tumour size reached approximately 400 mm$^3$ half of the mice were treated with CPA via intraperitoneal injection at 140 mg/kg. untreated mice were sacrificed when tumour volume reached around 1500 mm$^3$.

FIG. 14 shows that the effect of CPA on tumour cells expressing CYP2B6TM-RED was dramatic. CPA had only a modest effect on the uninfected tumour cells and did not produce an overall reduction in tumour volume. Tumour volume continued to increase after initial CPA treatment, followed by a slight reduction, but no overall reduction in tumour size was seen even after 4 weeks of treatment. Moreover; after the fourth and last CPA injection, tumor volume again began to increase dramatically.

In contrast, CPA treatment of CYP2B6TM-RED-infected tumour cells resulted in a dramatic decrease in tumour volume. A rapid regression was seen within 48 hours of treatment, and by 3 weeks of treatment the tumours had almost vanished. Three weeks after le last CPA injection, tumours remain undetectable.

The inventors have shown that the triple mutant CYP2B6 protein not only has a greatly improved catalytic activity compared to wild-type, but also has a greater effect on CPA-induced cytotoxicity than does the wild-type protein. Moreover, the triple mutant protein continues to show these improved effects in the context of a fusion protein with NADPH cytochrome p450 reductase. Both the triple mutant protein alone and the triple mutant-NADPH cytochrome p450 reductase fusion proteins are thus of great potential use in prodrug enzyme therapy.

SEQUENCE LISTING

```
<160> NUMBER OF SEQ ID NOS: 4

<210> SEQ ID NO 1
<211> LENGTH: 491
<212> TYPE: PRT
<213> ORGANISM: Homo sapiens

<400> SEQUENCE: 1

Met Glu Leu Ser Val Leu Leu Phe Leu Ala Leu Leu Thr Gly Leu Leu
1               5                   10                  15

Leu Leu Leu Val Gln Arg His Pro Asn Thr His Asp Arg Leu Pro Pro
                20                  25                  30

Gly Pro Arg Pro Leu Pro Leu Leu Gly Asn Leu Leu Gln Met Asp Arg
            35                  40                  45

Arg Gly Leu Leu Lys Ser Phe Leu Arg Phe Arg Glu Lys Tyr Gly Asp
        50                  55                  60

Val Phe Thr Val His Leu Gly Pro Arg Pro Val Val Met Leu Cys Gly
65                  70                  75                  80

Val Glu Ala Ile Arg Glu Ala Leu Val Asp Lys Ala Glu Ala Phe Ser
                85                  90                  95
```

Gly Arg Gly Lys Ile Ala Met Val Asp Pro Phe Phe Arg Gly Tyr Gly
                100                 105                 110

Val Val Phe Ala Asn Gly Asn Arg Trp Lys Val Leu Arg Phe Ser
            115                 120                 125

Val Thr Thr Met Arg Asp Phe Gly Met Gly Lys Arg Ser Val Glu Glu
            130                 135                 140

Arg Ile Gln Glu Glu Ala Gln Cys Leu Ile Glu Leu Arg Lys Ser
145                 150                 155                 160

Lys Gly Ala Leu Met Asp Pro Thr Phe Leu Phe Gln Ser Ile Thr Ala
                165                 170                 175

Asn Ile Ile Cys Ser Ile Val Phe Gly Lys Arg Phe His Tyr Gln Asp
            180                 185                 190

Gln Glu Phe Leu Lys Met Met Asn Leu Phe Tyr Gln Thr Phe Ser Leu
            195                 200                 205

Ile Ser Ser Val Phe Gly Gln Leu Phe Glu Leu Phe Ser Gly Phe Leu
        210                 215                 220

Lys Tyr Phe Pro Gly Ala His Arg Gln Val Tyr Lys Asn Leu Gln Glu
225                 230                 235                 240

Ile Asn Ala Tyr Ile Gly His Ser Val Glu Lys His Arg Glu Thr Leu
                245                 250                 255

Asp Pro Ser Ala Pro Lys Asp Leu Ile Asp Thr Tyr Leu Leu His Met
            260                 265                 270

Glu Lys Glu Lys Ser Asn Ala His Ser Glu Phe Ser His Gln Asn Leu
            275                 280                 285

Asn Leu Asn Thr Leu Ser Leu Phe Phe Ala Gly Thr Glu Thr Thr Ser
        290                 295                 300

Thr Thr Leu Arg Tyr Gly Phe Leu Leu Met Leu Lys Tyr Pro His Val
305                 310                 315                 320

Ala Glu Arg Val Tyr Arg Glu Ile Glu Gln Val Ile Gly Pro His Arg
                325                 330                 335

Pro Pro Glu Leu His Asp Arg Ala Lys Met Pro Tyr Thr Glu Ala Val
            340                 345                 350

Ile Tyr Glu Ile Gln Arg Phe Ser Asp Leu Leu Pro Met Gly Val Pro
        355                 360                 365

His Ile Val Thr Gln His Thr Ser Phe Arg Gly Tyr Ile Ile Pro Lys
        370                 375                 380

Asp Thr Glu Val Phe Leu Ile Leu Ser Thr Ala Leu His Asp Pro His
385                 390                 395                 400

Tyr Phe Glu Lys Pro Asp Ala Phe Asn Pro Asp His Phe Leu Asp Ala
                405                 410                 415

Asn Gly Ala Leu Lys Lys Thr Glu Ala Phe Ile Pro Phe Ser Leu Gly
            420                 425                 430

Lys Arg Ile Cys Leu Gly Glu Gly Ile Ala Arg Ala Glu Leu Phe Leu
        435                 440                 445

Phe Phe Thr Thr Ile Leu Gln Asn Phe Ser Met Ala Ser Pro Val Ala
            450                 455                 460

Pro Glu Asp Ile Asp Leu Thr Pro Gln Glu Cys Gly Trp Gly Lys Ile
465                 470                 475                 480

Pro Pro Thr Tyr Gln Ile Arg Phe Leu Pro Arg
                485                 490

<210> SEQ ID NO 2
<211> LENGTH: 680

<212> TYPE: PRT
<213> ORGANISM: Homo sapiens

<400> SEQUENCE: 2

Met Ile Asn Met Gly Asp Ser His Val Asp Thr Ser Ser Thr Val Ser
1               5                   10                  15

Glu Ala Val Ala Glu Val Ser Leu Phe Ser Met Thr Asp Met Ile
            20                  25                  30

Leu Phe Ser Leu Ile Val Gly Leu Leu Thr Tyr Trp Phe Leu Phe Arg
            35                  40                  45

Lys Lys Lys Glu Glu Val Pro Glu Phe Thr Lys Ile Gln Thr Leu Thr
            50                  55                  60

Ser Ser Val Arg Glu Ser Ser Phe Val Glu Lys Met Lys Lys Thr Gly
65                  70                  75                  80

Arg Asn Ile Ile Val Phe Tyr Gly Ser Gln Thr Gly Thr Ala Glu Glu
                85                  90                  95

Phe Ala Asn Arg Leu Ser Lys Asp Ala His Arg Tyr Gly Met Arg Gly
            100                 105                 110

Met Ser Ala Asp Pro Glu Glu Tyr Asp Leu Ala Asp Leu Ser Ser Leu
            115                 120                 125

Pro Glu Ile Asp Asn Ala Leu Val Val Phe Cys Met Ala Thr Tyr Gly
            130                 135                 140

Glu Gly Asp Pro Thr Asp Asn Ala Gln Asp Phe Tyr Asp Trp Leu Gln
145                 150                 155                 160

Glu Thr Asp Val Asp Leu Ser Gly Val Lys Phe Ala Val Phe Gly Leu
                165                 170                 175

Gly Asn Lys Thr Tyr Glu His Phe Asn Ala Met Gly Lys Tyr Val Asp
            180                 185                 190

Lys Arg Leu Glu Gln Leu Gly Ala Gln Arg Ile Phe Glu Leu Gly Leu
            195                 200                 205

Gly Asp Asp Asp Gly Asn Leu Glu Glu Asp Phe Ile Thr Trp Arg Glu
            210                 215                 220

Gln Phe Trp Pro Ala Val Cys Glu His Phe Gly Val Glu Ala Thr Gly
225                 230                 235                 240

Glu Glu Ser Ser Ile Arg Gln Tyr Glu Leu Val Val His Thr Asp Ile
                245                 250                 255

Asp Ala Ala Lys Val Tyr Met Gly Glu Met Gly Arg Leu Lys Ser Tyr
            260                 265                 270

Glu Asn Gln Lys Pro Pro Phe Asp Ala Lys Asn Pro Phe Leu Ala Ala
            275                 280                 285

Val Thr Thr Asn Arg Lys Leu Asn Gln Gly Thr Glu Arg His Leu Met
            290                 295                 300

His Leu Glu Leu Asp Ile Ser Ser Ser Lys Ile Arg Tyr Glu Ser Gly
305                 310                 315                 320

Asp His Val Ala Val Tyr Pro Ala Asn Asp Ser Ala Leu Val Asn Gln
                325                 330                 335

Leu Gly Lys Ile Leu Gly Ala Asp Leu Asp Val Val Met Ser Leu Asn
            340                 345                 350

Asn Leu Asp Glu Glu Ser Asn Lys Lys His Pro Phe Pro Cys Pro Thr
            355                 360                 365

Ser Tyr Arg Thr Ala Leu Thr Tyr Tyr Leu Asp Ile Thr Asn Pro Pro
            370                 375                 380

Arg Thr Asn Val Leu Tyr Glu Leu Ala Gln Tyr Ala Ser Glu Pro Ser
385                 390                 395                 400

Glu Gln Glu Leu Leu Arg Lys Met Ala Ser Ser Ser Gly Glu Gly Lys
            405                 410                 415

Glu Leu Tyr Leu Ser Trp Val Val Glu Ala Arg Arg His Ile Leu Ala
            420                 425                 430

Ile Leu Gln Asp Cys Pro Ser Leu Arg Pro Pro Ile Asp His Leu Cys
            435                 440                 445

Glu Leu Leu Pro Arg Leu Gln Ala Arg Tyr Tyr Ser Ile Ala Ser Ser
450                 455                 460

Ser Lys Val His Pro Asn Ser Val His Ile Cys Ala Val Val Val Glu
465                 470                 475                 480

Tyr Glu Thr Lys Ala Gly Arg Ile Asn Lys Gly Val Ala Thr Asn Trp
            485                 490                 495

Leu Arg Ala Lys Glu Pro Ala Gly Glu Asn Gly Gly Arg Ala Leu Val
            500                 505                 510

Pro Met Phe Val Arg Lys Ser Gln Phe Arg Leu Pro Phe Lys Ala Thr
            515                 520                 525

Thr Pro Val Ile Met Val Gly Pro Gly Thr Gly Val Ala Pro Phe Ile
            530                 535                 540

Gly Phe Ile Gln Glu Arg Ala Trp Leu Arg Gln Gln Gly Lys Glu Val
545                 550                 555                 560

Gly Glu Thr Leu Leu Tyr Tyr Gly Cys Arg Arg Ser Asp Glu Asp Tyr
            565                 570                 575

Leu Tyr Arg Glu Glu Leu Ala Gln Phe His Arg Asp Gly Ala Leu Thr
            580                 585                 590

Gln Leu Asn Val Ala Phe Ser Arg Glu Gln Ser His Lys Val Tyr Val
            595                 600                 605

Gln His Leu Leu Lys Gln Asp Arg Glu His Leu Trp Lys Leu Ile Glu
            610                 615                 620

Gly Gly Ala His Ile Tyr Val Cys Gly Asp Ala Arg Asn Met Ala Arg
625                 630                 635                 640

Asp Val Gln Asn Thr Phe Tyr Asp Ile Val Ala Glu Leu Gly Ala Met
            645                 650                 655

Glu His Ala Gln Ala Val Asp Tyr Ile Lys Lys Leu Met Thr Lys Gly
            660                 665                 670

Arg Tyr Ser Leu Asp Val Trp Ser
            675                 680

<210> SEQ ID NO 3
<211> LENGTH: 1148
<212> TYPE: PRT
<213> ORGANISM: Artificial
<220> FEATURE:
<223> OTHER INFORMATION: Synthetic fusion protein with 5ST linker

<400> SEQUENCE: 3

Met Glu Leu Ser Val Leu Leu Phe Leu Ala Leu Leu Thr Gly Leu Leu
1               5                   10                  15

Leu Leu Leu Val Gln Arg His Pro Asn Thr His Asp Arg Leu Pro Pro
            20                  25                  30

Gly Pro Arg Pro Leu Pro Leu Leu Gly Asn Leu Leu Gln Met Asp Arg
            35                  40                  45

Arg Gly Leu Leu Lys Ser Phe Leu Arg Phe Arg Glu Lys Tyr Gly Asp
            50                  55                  60

Val Phe Thr Val His Leu Gly Pro Arg Pro Val Val Met Leu Cys Gly
65                  70                  75                  80

```
Val Glu Ala Ile Arg Glu Ala Leu Val Asp Lys Ala Glu Ala Phe Ser
                85                  90                  95
Gly Arg Gly Lys Ile Ala Met Val Asp Pro Phe Phe Arg Gly Tyr Gly
            100                 105                 110
Val Val Phe Ala Asn Gly Asn Arg Trp Lys Val Leu Arg Arg Phe Ser
        115                 120                 125
Val Thr Thr Met Arg Asp Phe Gly Met Gly Lys Arg Ser Val Glu Glu
130                 135                 140
Arg Ile Gln Glu Glu Ala Gln Cys Leu Ile Glu Glu Leu Arg Lys Ser
145                 150                 155                 160
Lys Gly Ala Leu Met Asp Pro Thr Phe Leu Phe Gln Ser Ile Thr Ala
                165                 170                 175
Asn Ile Ile Cys Ser Ile Val Phe Gly Lys Arg Phe His Tyr Gln Asp
            180                 185                 190
Gln Glu Phe Leu Lys Met Met Asn Leu Phe Tyr Gln Thr Phe Ser Leu
        195                 200                 205
Ile Ser Ser Val Phe Gly Gln Leu Phe Glu Leu Phe Ser Gly Phe Leu
210                 215                 220
Lys Tyr Phe Pro Gly Ala His Arg Gln Val Tyr Lys Asn Leu Gln Glu
225                 230                 235                 240
Ile Asn Ala Tyr Ile Gly His Ser Val Glu Lys His Arg Glu Thr Leu
                245                 250                 255
Asp Pro Ser Ala Pro Lys Asp Leu Ile Asp Thr Tyr Leu Leu His Met
            260                 265                 270
Glu Lys Glu Lys Ser Asn Ala His Ser Glu Phe Ser His Gln Asn Leu
        275                 280                 285
Asn Leu Asn Thr Leu Ser Leu Phe Phe Ala Gly Thr Glu Thr Thr Ser
290                 295                 300
Thr Thr Leu Arg Tyr Gly Phe Leu Leu Met Leu Lys Tyr Pro His Val
305                 310                 315                 320
Ala Glu Arg Val Tyr Arg Glu Ile Glu Gln Val Ile Gly Pro His Arg
                325                 330                 335
Pro Pro Glu Leu His Asp Arg Ala Lys Met Pro Tyr Thr Glu Ala Val
            340                 345                 350
Ile Tyr Glu Ile Gln Arg Phe Ser Asp Leu Leu Pro Met Gly Val Pro
        355                 360                 365
His Ile Val Thr Gln His Thr Ser Phe Arg Gly Tyr Ile Ile Pro Lys
370                 375                 380
Asp Thr Glu Val Phe Leu Ile Leu Ser Thr Ala Leu His Asp Pro His
385                 390                 395                 400
Tyr Phe Glu Lys Pro Asp Ala Phe Asn Pro Asp His Phe Leu Asp Ala
                405                 410                 415
Asn Gly Ala Leu Lys Lys Thr Glu Ala Phe Ile Pro Phe Ser Leu Gly
            420                 425                 430
Lys Arg Ile Cys Leu Gly Glu Gly Ile Ala Arg Ala Glu Leu Phe Leu
        435                 440                 445
Phe Phe Thr Thr Ile Leu Gln Asn Phe Ser Met Ala Ser Pro Val Ala
450                 455                 460
Pro Glu Asp Ile Asp Leu Thr Pro Gln Glu Cys Gly Trp Gly Lys Ile
465                 470                 475                 480
Pro Pro Thr Tyr Gln Ile Arg Phe Leu Pro Ser Ser Ser Ser Ser Thr
                485                 490                 495
```

```
Ser Met Thr Asp Met Ile Leu Phe Ser Leu Ile Val Gly Leu Leu Thr
            500                 505                 510
Tyr Trp Phe Leu Phe Arg Lys Lys Glu Glu Val Pro Glu Phe Thr
        515                 520                 525
Lys Ile Gln Thr Leu Thr Ser Ser Val Arg Glu Ser Ser Phe Val Glu
        530                 535                 540
Lys Met Lys Lys Thr Gly Arg Asn Ile Ile Val Phe Tyr Gly Ser Gln
545                 550                 555                 560
Thr Gly Thr Ala Glu Glu Phe Ala Asn Arg Leu Ser Lys Asp Ala His
                565                 570                 575
Arg Tyr Gly Met Arg Gly Met Ser Ala Asp Pro Glu Glu Tyr Asp Leu
            580                 585                 590
Ala Asp Leu Ser Ser Leu Pro Glu Ile Asp Asn Ala Leu Val Val Phe
            595                 600                 605
Cys Met Ala Thr Tyr Gly Glu Gly Asp Pro Thr Asp Asn Ala Gln Asp
        610                 615                 620
Phe Tyr Asp Trp Leu Gln Glu Thr Asp Val Asp Leu Ser Gly Val Lys
625                 630                 635                 640
Phe Ala Val Phe Gly Leu Gly Asn Lys Thr Tyr Glu His Phe Asn Ala
                645                 650                 655
Met Gly Lys Tyr Val Asp Lys Arg Leu Glu Gln Leu Gly Ala Gln Arg
            660                 665                 670
Ile Phe Glu Leu Gly Leu Gly Asp Asp Gly Asn Leu Glu Glu Asp
            675                 680                 685
Phe Ile Thr Trp Arg Glu Gln Phe Trp Pro Ala Val Cys Glu His Phe
        690                 695                 700
Gly Val Glu Ala Thr Gly Glu Glu Ser Ser Ile Arg Gln Tyr Glu Leu
705                 710                 715                 720
Val Val His Thr Asp Ile Asp Ala Ala Lys Val Tyr Met Gly Glu Met
                725                 730                 735
Gly Arg Leu Lys Ser Tyr Glu Asn Gln Lys Pro Pro Phe Asp Ala Lys
            740                 745                 750
Asn Pro Phe Leu Ala Ala Val Thr Thr Asn Arg Lys Leu Asn Gln Gly
            755                 760                 765
Thr Glu Arg His Leu Met His Leu Glu Leu Asp Ile Ser Asp Ser Lys
        770                 775                 780
Ile Arg Tyr Glu Ser Gly Asp His Val Ala Val Tyr Pro Ala Asn Asp
785                 790                 795                 800
Ser Ala Leu Val Asn Gln Leu Gly Lys Ile Leu Gly Ala Asp Leu Asp
                805                 810                 815
Val Val Met Ser Leu Asn Asn Leu Asp Glu Glu Ser Asn Lys Lys His
            820                 825                 830
Pro Phe Pro Cys Pro Thr Ser Tyr Arg Thr Ala Leu Thr Tyr Tyr Leu
        835                 840                 845
Asp Ile Thr Asn Pro Pro Arg Thr Asn Val Leu Tyr Glu Leu Ala Gln
        850                 855                 860
Tyr Ala Ser Glu Pro Ser Glu Gln Glu Leu Leu Arg Lys Met Ala Ser
865                 870                 875                 880
Ser Ser Gly Glu Gly Lys Glu Leu Tyr Leu Ser Trp Val Val Glu Ala
                885                 890                 895
Arg Arg His Ile Leu Ala Ile Leu Gln Asp Cys Pro Ser Leu Arg Pro
            900                 905                 910
Pro Ile Asp His Leu Cys Glu Leu Leu Pro Arg Leu Gln Ala Arg Tyr
```

```
                    915                 920                 925

Tyr Ser Ile Ala Ser Ser Lys Val His Pro Asn Ser Val His Ile
    930                 935                 940

Cys Ala Val Val Glu Tyr Glu Thr Lys Ala Gly Arg Ile Asn Lys
945                 950                 955                 960

Gly Val Ala Thr Asn Trp Leu Arg Ala Lys Glu Pro Ala Gly Glu Asn
                965                 970                 975

Gly Gly Arg Ala Leu Val Pro Met Phe Val Arg Lys Ser Gln Phe Arg
            980                 985                 990

Leu Pro Phe Lys Ala Thr Thr Pro Val Ile Met Val Gly Pro Gly Thr
        995                 1000                1005

Gly Val Ala Pro Phe Ile Gly Phe Ile Gln Glu Arg Ala Trp Leu
    1010                1015                1020

Arg Gln Gln Gly Lys Glu Val Gly Glu Thr Leu Leu Tyr Tyr Gly
    1025                1030                1035

Cys Arg Arg Ser Asp Glu Asp Tyr Leu Tyr Arg Glu Glu Leu Ala
    1040                1045                1050

Gln Phe His Arg Asp Gly Ala Leu Thr Gln Leu Asn Val Ala Phe
    1055                1060                1065

Ser Arg Glu Gln Ser His Lys Val Tyr Val Gln His Leu Leu Lys
    1070                1075                1080

Gln Asp Arg Glu His Leu Trp Lys Leu Ile Glu Gly Gly Ala His
    1085                1090                1095

Ile Tyr Val Cys Gly Asp Ala Arg Asn Met Ala Arg Asp Val Gln
    1100                1105                1110

Asn Thr Phe Tyr Asp Ile Val Ala Glu Leu Gly Ala Met Glu His
    1115                1120                1125

Ala Gln Ala Val Asp Tyr Ile Lys Lys Leu Met Thr Lys Gly Arg
    1130                1135                1140

Tyr Ser Leu Asp Val
    1145

<210> SEQ ID NO 4
<211> LENGTH: 491
<212> TYPE: PRT
<213> ORGANISM: Homo sapiens

<400> SEQUENCE: 4

Met Glu Leu Ser Val Leu Leu Phe Leu Ala Leu Leu Thr Gly Leu Leu
1               5                   10                  15

Leu Leu Leu Val Gln Arg His Pro Asn Thr His Asp Arg Leu Pro Pro
            20                  25                  30

Gly Pro Arg Pro Leu Pro Leu Leu Gly Asn Leu Leu Gln Met Asp Arg
        35                  40                  45

Arg Gly Leu Leu Lys Ser Phe Leu Arg Phe Arg Glu Lys Tyr Gly Asp
    50                  55                  60

Val Phe Thr Val His Leu Gly Pro Arg Pro Val Val Met Leu Cys Gly
65                  70                  75                  80

Val Glu Ala Ile Arg Glu Ala Leu Val Asp Lys Ala Glu Ala Phe Ser
                85                  90                  95

Gly Arg Gly Lys Ile Ala Met Val Asp Pro Phe Phe Arg Gly Tyr Gly
            100                 105                 110

Val Ile Phe Ala Asn Gly Asn Arg Trp Lys Val Leu Arg Arg Phe Ser
        115                 120                 125
```

```
Val Thr Thr Met Arg Asp Phe Gly Met Gly Lys Arg Ser Val Glu Glu
    130             135             140
Arg Ile Gln Glu Glu Ala Gln Cys Leu Ile Glu Glu Leu Arg Lys Ser
145             150             155             160
Lys Gly Ala Leu Met Asp Pro Thr Phe Leu Phe Gln Ser Ile Thr Ala
            165             170             175
Asn Ile Ile Cys Ser Ile Val Phe Gly Lys Arg Phe His Tyr Gln Asp
        180             185             190
Gln Glu Phe Leu Lys Met Leu Asn Leu Phe Tyr Gln Thr Phe Ser Leu
        195             200             205
Ile Ser Ser Val Phe Gly Gln Leu Phe Glu Leu Phe Ser Gly Phe Leu
210             215             220
Lys Tyr Phe Pro Gly Ala His Arg Gln Val Tyr Lys Asn Leu Gln Glu
225             230             235             240
Ile Asn Ala Tyr Ile Gly His Ser Val Glu Lys His Arg Glu Thr Leu
            245             250             255
Asp Pro Ser Ala Pro Lys Asp Leu Ile Asp Thr Tyr Leu Leu His Met
            260             265             270
Glu Lys Glu Lys Ser Asn Ala His Ser Glu Phe Ser His Gln Asn Leu
        275             280             285
Asn Leu Asn Thr Leu Ser Leu Phe Phe Ala Gly Thr Glu Thr Thr Ser
        290             295             300
Thr Thr Leu Arg Tyr Gly Phe Leu Leu Met Leu Lys Tyr Pro His Val
305             310             315             320
Ala Glu Arg Val Tyr Arg Glu Ile Glu Gln Val Ile Gly Pro His Arg
            325             330             335
Pro Pro Glu Leu His Asp Arg Ala Lys Met Pro Tyr Thr Glu Ala Val
            340             345             350
Ile Tyr Glu Ile Gln Arg Phe Ser Asp Leu Leu Pro Met Gly Val Pro
        355             360             365
His Ile Val Thr Gln His Thr Ser Phe Arg Gly Tyr Ile Ile Pro Lys
        370             375             380
Asp Thr Glu Val Phe Leu Ile Leu Ser Thr Ala Leu His Asp Pro His
385             390             395             400
Tyr Phe Glu Lys Pro Asp Ala Phe Asn Pro Asp His Phe Leu Asp Ala
            405             410             415
Asn Gly Ala Leu Lys Lys Thr Glu Ala Phe Ile Pro Phe Ser Leu Gly
            420             425             430
Lys Arg Ile Cys Leu Gly Glu Gly Ile Ala Arg Ala Glu Leu Phe Leu
            435             440             445
Phe Phe Thr Thr Ile Leu Gln Asn Phe Ser Met Ala Ser Pro Val Ala
        450             455             460
Pro Glu Asp Ile Asp Leu Thr Pro Gln Glu Cys Gly Val Gly Lys Ile
465             470             475             480
Pro Pro Thr Tyr Gln Ile Arg Phe Leu Pro Arg
            485             490
```

Figure 5:
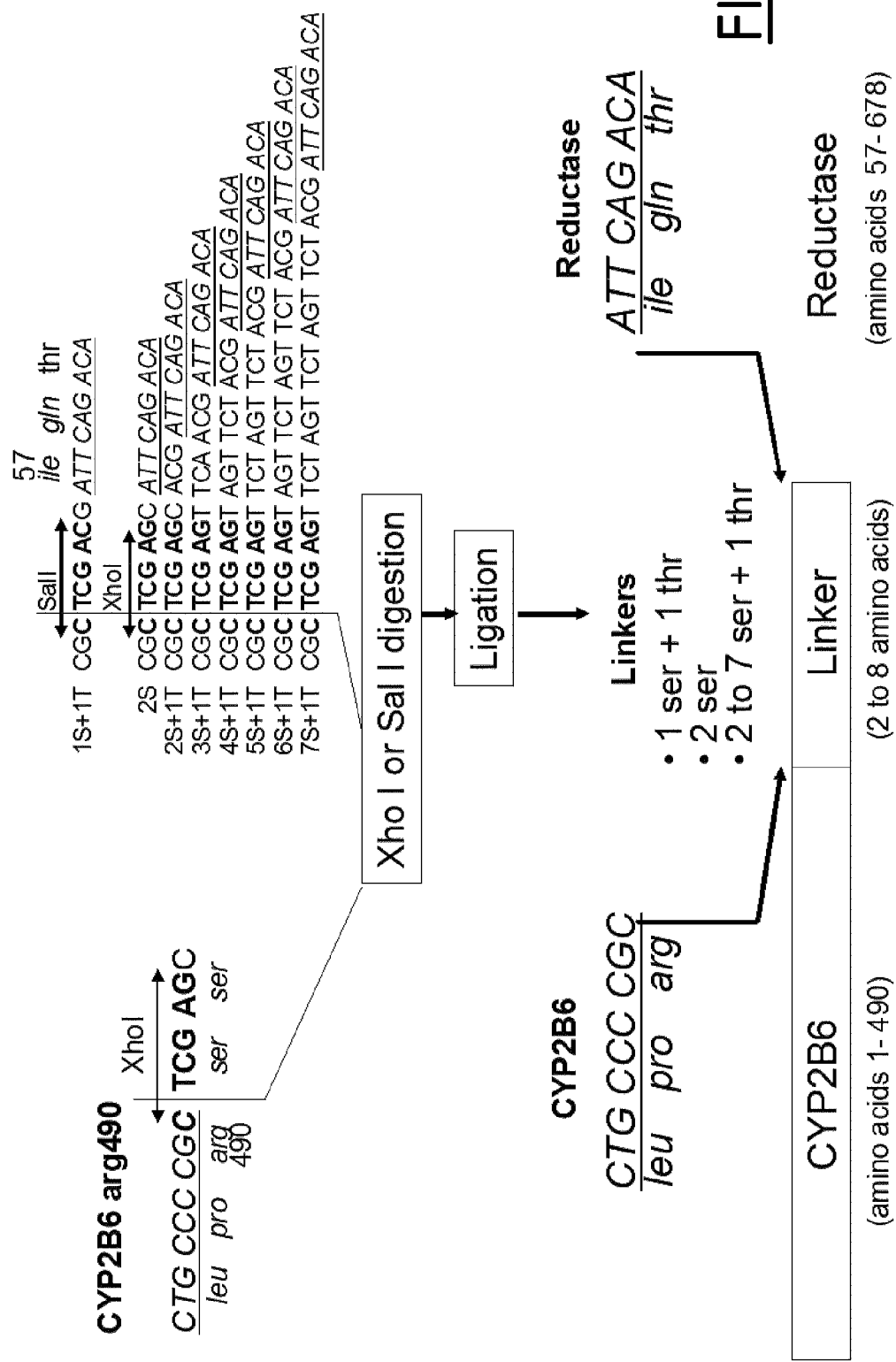
FIG. 5 shows the cloning strategy for construction of the CYP2B6TM-RED fusion proteins, including the insertion of different linker sequences.

The invention claimed is:

1. An isolated nucleic acid encoding a CYP2B6 protein comprising
   (i) the amino acid sequence of FIG. 1 (SEQ ID NO: 1), or
   (ii) a variant or fragment of (i), wherein said variant or fragment is at least 90% identical to residues 1-490 of FIG. 1 (SEQ ID NO: 1) and comprises residues 114V, 199M and 477W as shown in FIG. 1 (SEQ ID NO: 1) and said variant or fragment has an affinity for CPA that is at least 4 times greater than the affinity for CPA of the wild-type protein as shown in FIG. 5 (SEQ ID NO: 5), or a fusion protein comprising the CYP2B6 protein according to (i) or (ii) and a NADPH-cytochrome P450 reductase protein as shown in FIG. 2/SEQ ID NO: 2, or variant or fragment thereof, wherein said NADPH-cytochrome P450 reductase protein, variant or fragment thereof is at least 90% identical to residues 57-678 of FIG. 2 (SEQ ID NO: 2).

2. A vector comprising the nucleic acid of claim 1.

3. A host cell comprising the vector of claim 2.

4. A method of making a protein, comprising culturing a host cell comprising a vector comprising a nucleic acid encoding
a CYP2B6 protein comprising
(i) the amino acid sequence of FIG. 1 (SEQ ID NO: 1), or
(ii) a variant or fragment of (i), wherein said variant or fragment is at least 90% identical to residues 1-490 of FIG. 1 (SEQ ID NO: 1) and comprises residues 114V, 199M and 477W as shown in FIG. 1 (SEQ ID NO: 1) and said variant or fragment has an affinity for CPA that is at least 4 times greater than the affinity for CPA of the wild-type protein as shown in FIG. 5 (SEQ ID NO: 5), or
a fusion protein comprising the CYP2B6 protein according to (i) or (ii) and a NADPH-cytochrome P450 reductase protein as shown in FIG. 2/SEQ ID NO: 2, or variant or fragment thereof, wherein said NADPH-cytochrome P450 reductase protein, variant or fragment thereof is at least 90% identical to residues 57-678 of FIG. 2 (SEQ ID NO: 2),
in cell culture conditions suitable for expression of said protein or said fusion protein.

5. The isolated nucleic acid according to claim 1, wherein said NADPH-cytochrome P450 reductase protein, variant or fragment thereof
(i) differs from SEQ ID NO: 2 by less than 20 conservative amino acid substitutions; and/or
(ii) differs from SEQ ID NO: 2 by less than 20 amino acid deletions or additions; or
(iii) comprises amino acids 57-678 of FIG. 2 (SEQ ID NO: 2).

6. The isolated nucleic acid according to claim 1, wherein said CYP2B6 protein, variant or fragment thereof
(i) differs from SEQ ID NO: 1 by less than 20 conservative amino acid substitutions;
and/or
(ii) differs from SEQ ID NO: 1 by less than 20 amino acid deletions or additions; or
(iii) comprises amino acids 1-490 of FIG. 1 (SEQ ID NO: 1).

7. The isolated nucleic acid according to claim 1, wherein said CYP2B6 protein, variant or fragment thereof has at least a 7.9 times increase in CPA-4OH catalytic efficiency ($V_{MAX}/K_M$) in comparison to the wild-type protein.

8. The isolated nucleic acid according to claim 1, wherein the CYP2B6 protein is upstream of the NADPH-cytochrome P450 reductase.

9. The isolated nucleic acid according to claim 1, wherein the mutant human CYP2B6 protein and the NADPH-cytochrome P450 reductase are separated by a linker.

10. The isolated nucleic acid according to claim 9, wherein the linker consists of 3 to 30 nucleotide residues.

11. The isolated nucleic acid according to claim 9, wherein said isolated nucleic acid has the sequence of FIG. 3 (SEQ ID NO: 3).

* * * * *